(12) United States Patent
Hattori et al.

(10) Patent No.: US 7,842,514 B2
(45) Date of Patent: Nov. 30, 2010

(54) PARTICLE MANIPULATION UNIT, CHIP AND DETECTION DEVICE HAVING THE SAME, MOUNTED THEREON, AND METHODS OF SEPARATING, CAPTURING AND DETECTING PROTEINS

(75) Inventors: Wataru Hattori, Tokyo (JP); Masakazu Baba, Tokyo (JP); Toru Sano, Tokyo (JP); Kazuhiro Iida, Tokyo (JP); Hisao Kawaura, Tokyo (JP); Noriyuki Iguchi, Tokyo (JP); Hiroko Someya, Tokyo (JP)

(73) Assignee: NEC Corporation, Tokyo (JP)

( * ) Notice: Subject to any disclaimer, the term of this patent is extended or adjusted under 35 U.S.C. 154(b) by 979 days.

(21) Appl. No.: 10/537,292

(22) PCT Filed: Nov. 25, 2003

(86) PCT No.: PCT/JP03/15031

§ 371 (c)(1),
(2), (4) Date: Jun. 2, 2005

(87) PCT Pub. No.: WO2004/051230

PCT Pub. Date: Jun. 17, 2004

(65) Prior Publication Data

US 2006/0035386 A1    Feb. 16, 2006

(30) Foreign Application Priority Data

| Dec. 2, 2002 | (JP) | ................................ 2002-349492 |
| May 8, 2003 | (JP) | ................................ 2003-130834 |
| Nov. 19, 2003 | (JP) | ................................ 2003-389566 |

(51) Int. Cl.
*G01N 33/558* (2006.01)

(52) U.S. Cl. .................................................. 436/514

(58) Field of Classification Search ................ 436/514, 436/4, 7.92, 287.1–287.3, 288.4–288.6
See application file for complete search history.

(56) References Cited

U.S. PATENT DOCUMENTS

| 5,716,526 | A | * | 2/1998 | Kelemen et al. ............. 210/650 |
| 6,086,825 | A | * | 7/2000 | Sundberg et al. ............ 422/100 |
| 6,235,471 | B1 | * | 5/2001 | Knapp et al. .................. 435/6 |
| 6,729,352 | B2 | * | 5/2004 | O'Connor et al. ............ 137/827 |
| 7,195,872 | B2 | * | 3/2007 | Agrawal et al. ................ 435/6 |
| 7,534,601 | B2 | * | 5/2009 | Wikswo et al. ............ 435/289.1 |
| 2002/0072243 | A1 | | 6/2002 | Craighead et al. | |

FOREIGN PATENT DOCUMENTS

| JP | 07-198680 | | 8/1995 |
| JP | 9-504362 | | 4/1997 |
| JP | 09-509498 | | 9/1997 |
| JP | 10-506991 | | 7/1998 |
| JP | 2001-183363 | | 7/2001 |
| JP | 2001-258868 | | 9/2001 |
| JP | 2001-515216 | | 9/2001 |
| JP | 2002-515820 | | 5/2002 |
| JP | 2002-195982 | | 7/2002 |
| JP | 2002-524755 | | 8/2002 |
| JP | 2002-286594 | | 10/2002 |
| JP | 2002-292600 | | 10/2002 |
| WO | 96/14934 | | 5/1996 |
| WO | 97/04297 | | 2/1997 |
| WO | WO9813131 | * | 4/1998 |
| WO | 01/38865 | | 5/2001 |
| WO | 01/47638 | | 7/2001 |
| WO | WO 02/23180 | | 3/2002 |

OTHER PUBLICATIONS

Iida, Kawaura, Iguchi, Sano, Baba, Dai 63 kai Extended Abstracts; The Japan Society of Applied Physics, separate vol. 3, Sep. 24, 2002, p. 1147 (25a-R-9).

K. Iida, H. Kawaura, N. Iguchi, T. Sano, M. Baba, Sixth International Conference on Miniaturized Chemical and Biochemical Analysis Systems (Micro Total Analysis Systems 2002), Nov. 3, 2002, vol. 2, pp. 627 to 629.

Sano, Baba, Iguchi, Iida, Kawaura, Sakamoto, Dai 63 Kai Extended Abstracts; The Japan Society of Applied Physics, separate vol. 3, Sep. 24, 2002, p. 1146 (25a-R-8).

Chia-Fu Chou et al., Proceedings of the National Academy of Sciences of the Unites States of America, Nov. 23, 1999, vol. 96, No. 24, pp. 13762 to 13765.

Japanese Patent Office issued a Japanese Office Action dated Sep. 29, 2009, Application No. 2003-389566.

* cited by examiner

*Primary Examiner*—Ann Y Lam
(74) *Attorney, Agent, or Firm*—Young & Thompson

(57) ABSTRACT

A channel (1) formed in a substrate (41) branches into channels (2, 3) at a branch point (43). On this branch point, obstacles (8) having a columnar structure are aligned at certain intervals.

25 Claims, 24 Drawing Sheets

100 μm

FIG. 24
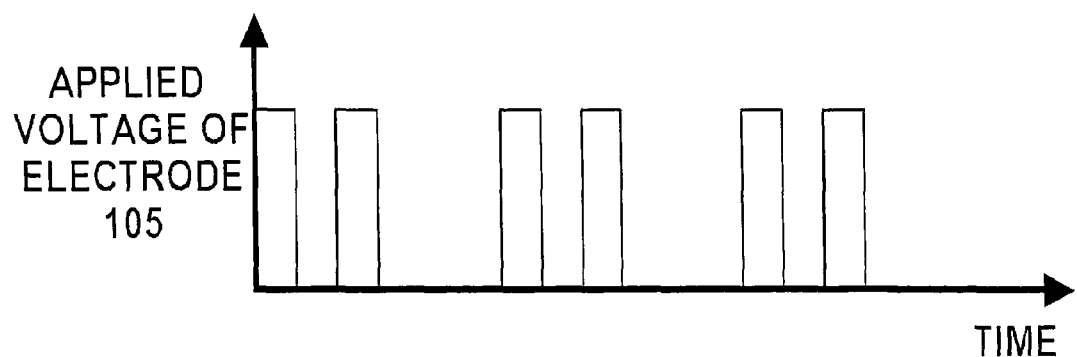
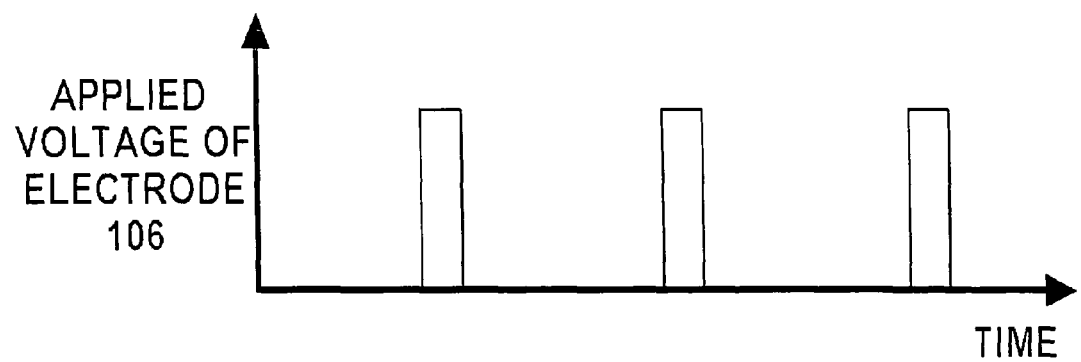

PARTICLE MANIPULATION UNIT, CHIP AND DETECTION DEVICE HAVING THE SAME, MOUNTED THEREON, AND METHODS OF SEPARATING, CAPTURING AND DETECTING PROTEINS

FIELD OF THE INVENTION

The present invention relates to a particle manipulation unit, a chip and a detection device having the same mounted thereon, and methods of separating, capturing and detecting proteins.

RELATED ART

With advancement in recent micro-electro-mechanical system (MEMS) technologies, trials have been made on particle treatment making use of micro-channels in particular in the field of biological MEMS. For example, there has been proposed a fractionation apparatus having obstacles for electrophoretic use fabricated therein by microfabrication technologies, in place of using a polymer gel (Patent Document 1). This raised industrial advantages in that it would be no more necessary to prepare polymer gels and would improve the reproducibility. The particle treatment apparatus using the micro-channel has, however, been suffering from a problem of extremely small capacity of the treatment.

As a solution for this problem, there has been proposed a method of continuously treating particles (Patent Document 2). The technique described in Patent Document 2 realizes continuous separation of biological molecules, which are kinds of the particle, by allowing migration of the biological molecules in a buffer solution under continuous flow of the buffer solution for electrophoresis, and under application of an electric field in the direction normal to the flow. The continuous treatment is successful in clearing a restriction of the extremely small treating capacity, by virtue of prolonged time of treatment.

Another trial has been made on adopting microfabrication technique for fabrication of the obstacles (Non-Patent Document 1). The method described in Non-Patent Document 1 continuously separates particles using a regular lattice of obstacles having an asymmetric geometry with respect to the flow.

The conventional techniques have, however, been suffering from problems below. The buffer solution in the technique described in Patent Document 2 is allowed to flow using a pump so as to proceed electrophoresis, and the flow rate determines the angle of separation, so that variation in the flow rate of the buffer solution due to the pulsating pump considerably varies the resolution.

The device described in Non-Patent Document 1, having the obstacles fixed therein, is more successful in carrying out stable separation as compared with the method described in Patent Document 2. It was, however, not easy to adopt the device to fine particles of molecular level, such as biological molecules, because the separation performance thereof depends on the geometry of the obstacles. For example, separation of particles having a particle size of as small as 50 nm or less, such as proteins, demands a higher level of accuracy in the geometry of obstacles, but it is difficult for the current microfabrication technology to fabricate such level of fine geometry with a satisfactory accuracy. Even for the case where particles having size of the order of millimeter, such as cells, are separated, there has also been requests on a high level of process accuracy for the obstacles in connection with size of particles to be separated, and realization of such process accuracy has demanded an expensive process technologies.

Patent Document 1: Published Japanese Translations of PCT International Publication for Patent Applications No. 9-504362;

Patent Document 2: Japanese Laid-Open Patent Publication No. 2002-195982;

Non-Patent Document: Chia-Fu Chou et al., Proceedings of the National Academy of Sciences of the United States of America (UNITED STATES), 1999, Vol. 96, No. 24, p. 13762-13765

SUMMARY OF THE INVENTION

The present invention was conceived after considering the above-described situations, and an object thereof is to provide a particle manipulation unit manipulating particle flow in liquid in a micro-channel, a chip, and a method of treating proteins.

According to the present invention, there is provided a particle manipulation unit comprising a substrate, and a channel formed on the substrate, comprising a first channel and a second channel branched out from the first channel, capable of manipulating direction of flow of particles flowing in a liquid in the channel, further comprising a permeation limiting zone limiting permeation of at least a part of the particles, disposed in the first channel in the vicinity of a branching point where one or more second channels are branched out from the first channel.

In the present invention, "particles" means molecules, atoms or assemblies having sizes of the order of millimeter or less, and typically include metal particles, semiconductor particles, polymer resins, cells and biological polymers. Of these, the biological polymers include protein, nucleic acid, polysaccharide, lipid and complexes of them. "Manipulation of particles" principally means operations for regulating direction and route of particle flow in the channel. Control of the particle flow enables various treatment including separation, condensation, dilution, desalting and solvent replacement.

The particle manipulation unit of the present invention has the limitative permeation zone in the channel. This makes it possible to limit migration, towards the downstream side, of the particles beyond the branching point where the first channel and the second channel branch from each other. Of the particles in the liquid, which came through first channel to reach the permeation limiting zone, only those having predetermined geometries and sizes can permeate through the permeation limiting zone, and guided towards the downstream side of the first channel. It is also made possible to manipulate the direction of flow of specific particles out of those contained in the fluid, that is, those incapable of permeateting through the permeation limiting zone, and to guide only such particles towards the second channel. In this way, the particle manipulation unit of the present invention makes it possible to readily and efficiently control direction of flow of the particles in the liquid.

In the particle manipulation unit of the present invention, the permeation limiting zone may be configured as having a plurality of obstacles arranged as being spaced from each other. This configuration makes it possible to separate the particles capable and incapable of permeateting through gaps between the obstacles, based on the surface property, geometry, size, deformation liability and so forth of the particles.

In the particle manipulation unit of the present invention, the gap between the adjacent obstacles may be set to a size allowing a part of the particles to permeate therethrough. This configuration makes it possible to exactly separate the particles contained in the liquid in the first channel, based on their geometries and sizes.

In the particle manipulation unit of the present invention, the obstacles may be arranged so that direction of force causing flow of the particles lies non-normal to, or non-parallel with direction of array of the obstacles at the front-most plane on the branching point side of the permeation limiting zone.

The "direction of array of the obstacles at the front-most plane on the branching point side of the permeation limiting zone" means the direction connecting the obstacles placed at the front-most plane, when the array of the obstacles is viewed from the downstream side of the channel. Aligning the direction of arrangement non-normal to the force causing flow of the particles makes it possible to suppress the deposition of the particles, incapable of permeate through the permeation limiting zone, in the vicinity of the permeation limiting zone, and to efficiently guide them into the second channel. Adoption of non-parallel arrangement can exactly allow permeation through the permeation limiting zone of the particles, out of those contained in the liquid, having geometries and sizes allowable for the permeation through the permeation limiting zone.

In the particle manipulation unit of the present invention, the plurality of obstacles are configured so as to control direction of flow of the particles, and so as to guide at least a part of the particles to either of the first channel and the second channel, depending on the arrangement thereof. This configuration makes it possible to guide the particles into the predetermined channels, making use of the arrangement of a plurality of obstacles. It is therefore made possible to exactly separate the particles guided into the first channel from those guided to the second channel.

In the particle manipulation unit of the present invention, the obstacles may periodically be arranged in a two-dimensional manner. This configuration allows the treatment with a still higher accuracy.

According to the present invention, there is provided a particle manipulation unit comprising a substrate, and a channel formed on the substrate, comprising a main channel, and one or more side channels branched out from the main channel towards the downstream side of the main channel, capable of manipulating direction of flow of particles flowing in a liquid in the channel, further comprises a flow control portion disposed on the upstream side of a branching point where one or more side channels are branched out from the main channel, the flow control portion controls direction of flow of the particles, and guides at least a part of the particles to either of the main channel and the side channel.

Because the flow control portion is disposed on the upstream side of the branching point where one or more side channels are branched out from the main channel, the particle manipulation unit of the present invention can guide the particles introduced to the branching point into either of the side channels, based on the surface property, geometry, size, deformation liability and so forth of the particles. It is therefore made possible to distribute the individual components in the liquid containing a plurality of particles into desired side channels.

In the particle manipulation unit of the present invention, the flow control portion may be configured as having a plurality of obstacles, the plurality of obstacles being configured so as to control direction of flow of the particles, and so as to guide at least a part of the particles to either of the main channel and the side channels, depending on the arrangement thereof. This configuration makes it possible to guide the particles into the predetermined channels, making use of the arrangement of a plurality of obstacles. It is therefore made possible to exactly separate the particles guided into the main channel from those guided to the side channels.

In the particle manipulation unit of the present invention, the flow control portion may be configured as having a plurality of obstacles periodically arranged therein. This configuration makes it possible to separate the particles capable and incapable of permeateting through gaps between the obstacles, based on the surface property, geometry, size, deformation liability and so forth of the particles.

In the particle manipulation unit of the present invention, a gap between the adjacent obstacles of the flow control portion in the direction of formation of the main channel may differ from that in the direction of formation of the side channel. The "gap between the adjacent obstacles", in connection to the direction of formation of the main channel or the side channels means a gap between the obstacles as viewed on a sectional plane taken normal to the direction of formation of the channel. By making difference between the gaps in the main channel and the gaps in the side channels, it is made possible to exactly distribute the particles in the flow control portion into the individual side channels and the main channel, based on their geometry, size and so forth.

According to the present invention, there is provided a particle manipulation unit comprising a substrate, and a channel formed on the substrate, capable of manipulating state of flow of particles flowing in the channel, the channel having a flow control portion which comprises trenches formed on the wall surface of the channel, guiding at least a part of the particles to a predetermined direction.

Because the flow control portion has the trenches formed therein, the particle manipulation unit of the present invention can selectively guide the particles capable of interacting with the trenches out of those contained in the liquid in the channel, to a desired direction based on geometry and direction of formation of the trenches, and depending on the magnitude of interaction with the trenches. It is therefore made possible to carry out predetermined processes such as separation, condensation, and so forth of specific components in the liquid containing a plurality of particles.

The state of flow in the context of the present invention typically include direction of flow and rate of flow.

The particle manipulation unit of the present invention may be configured as having the flow control portion having the trenches periodically formed on the wall surface of the channel. This configuration makes it possible to more exactly control flow of the particles, making use of the arrangement of the trenches formed on the wall surface of the channel making use of the arrangement of the flow channels.

In the particle manipulation unit of the present invention, the flow control portion may be configured as including a plurality of periodic patterns which differ in geometry of opening of the trenches or pitch of the trench. This configuration makes it possible to more precisely control flow of the particles.

In the particle manipulation unit of the present invention, the plurality of periodic patterns may be formed with mirror symmetry in the flow control portion. This configuration makes it possible to concentrate predetermined particle in the liquid into a specific region in the channel.

According to the present invention, there is provided a particle manipulation unit comprising a substrate, and a channel formed on the substrate, capable of manipulating direction of flow of particles flowing in the channel, the channel having, provided thereto, a permeation limiting zone limiting permeation therethrough of at least a part of the particles, the permeation limiting zone having a width of entrance narrower than the width of the permeation limiting zone, having a first drive means providing the particle flowing in the permeation limiting zone with a migration speed in one direction, and a second drive means providing a migration speed in other direction different from one direction, and the permeation limiting zone being provided with a plurality of obstacles arranged as being spaced from each other.

The particle manipulation unit of the present invention has, in the permeation limiting zone, the first drive means and the second drive means capable of making the particles move towards a plurality of directions which differ from each other. The channel is also provided with a plurality of obstacles. This makes it possible to stably separate the particles based on the surface property, geometry, size, deformation liability and so forth of the particles. The particles can exactly be separated, also because the width of entrance of the permeation limiting zone is configured as being narrower than the width of the permeation limiting zone.

In the present invention, the particles may be such as those containing any one of polymer resin, metal, semiconductor and biological molecules.

The particle manipulation unit of the present invention may be configured as having a function of separating the particles depending on their sizes.

The particle manipulation unit of the present invention may be configured as having a function of introducing a suspension, having said particles suspended therein, into the channel and diluting the suspension.

According to the present invention, there is provided a chip having the above-described particle manipulation unit. The chip of the present invention has functions of various treatment including separation, condensation, dilution, desalting and solvent replacement, through control of the particle flow. In one exemplary chip of the present invention, the particle manipulation unit may have a channel which comprises a first channel and a second channel branched out from the first channel, and may have a permeation limiting zone limiting permeation of at least a part of the particles, disposed in the first channel in the vicinity of a branching point where one or more second channels are branched out from the first channel.

In this configuration, the particles in the first channel are separated via the permeation limiting zone into the first channel and the second channel, realizing manipulation of direction of flow of the particles. The chip having thus-configured particle manipulation unit may have a sample introduction portion communicating with the first channel, on the upstream side of the permeation limiting zone. It is also allowable to introduce the sample containing the particles from other channel. On the other hand, the chip may have a sample discharge portion, or sample recovery portion, communicated with the first channel of the second channel, on the upstream side of the permeation limiting zone.

According to the present invention, there is provided a detection device comprising the chip and a detection unit for the particles.

In this detection device, the detection unit for the particles may be configured by a mass spectroscope.

According to the present invention, there is provided a method of separating proteins comprising two or more process steps respectively using separation means differing from each other, having, as one of the process steps separating proteins, a process step separating proteins using a chip having at least a function of continuously separating proteins.

According to the present invention, there is also provided a method of separating proteins comprising a process step roughly separating proteins, and a succeeding process step electrophoretically separating the roughly-separated proteins, wherein the process step roughly separating the proteins comprises a process step roughly separating proteins using a chip having at least a function of continuously separating the proteins.

According to the present invention, there is also provided a method of detecting proteins in which proteins are separated by the above-described method, the separated proteins are decomposed by protease treatment, and the decomposed products are identified using a mass spectroscope.

According to the present invention, there is also provided a method of capturing proteins in which proteins are separated using the chip of the present invention, and a target protein is captured from a suspension of a plurality of proteins, making use of affinity.

According to the present invention, there is still also provided a method of detecting proteins in which the target protein is captured by the above-described method of capturing proteins, the surface of the chip is washed, and the captured protein is identified using a mass spectroscope.

As described in the above, the present invention successfully realizes a particle manipulation unit capable of manipulating the particle flow in the liquid in the micro channel, a chip and a detector having the unit mounted thereon, and methods of separating, capturing and detecting proteins.

BRIEF DESCRIPTION OF THE DRAWINGS

The above and other objects, features and advantages of the present invention will be more apparent from the following description of preferred embodiments taken in conjunction with the accompanying drawings.

FIG. 24 is a drawing showing voltage applied to electrodes of the particle manipulation unit shown in FIG. 21.

DETAILED DESCRIPTION OF THE INVENTION

Figure 1:
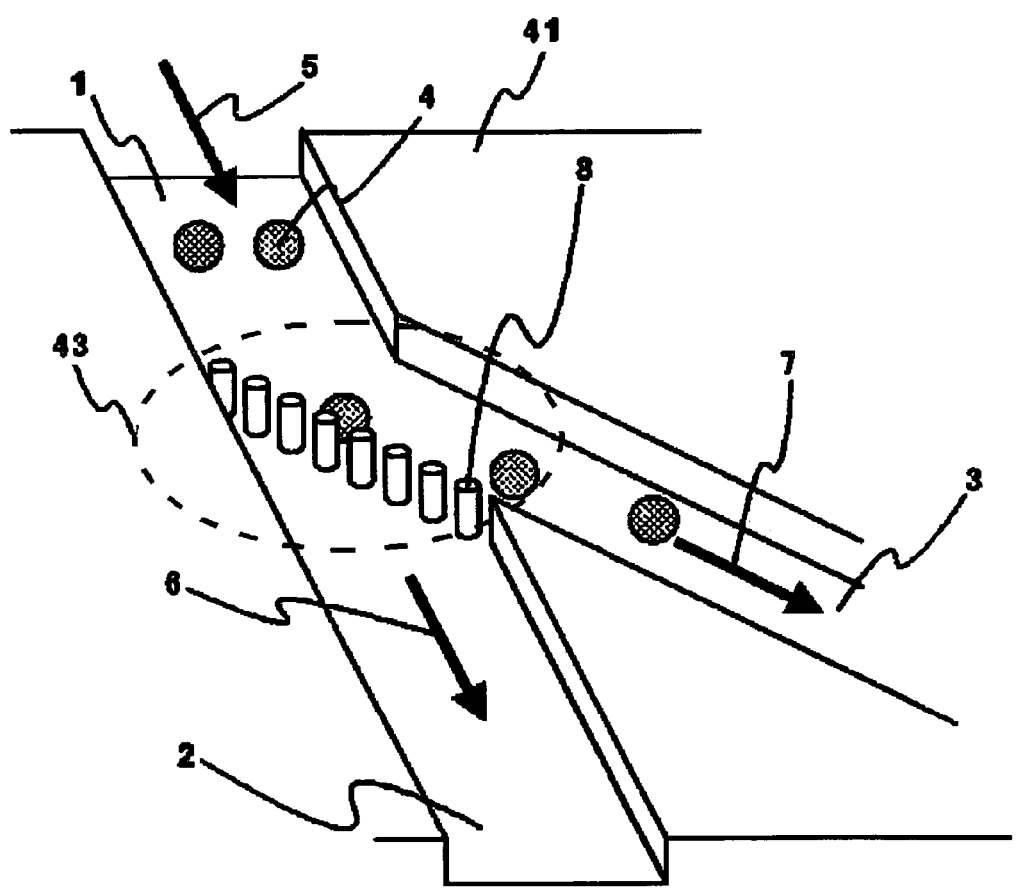
FIG. 1 is a perspective view showing an exemplary configuration of a particle manipulation unit of the present embodiment.

The following paragraphs will describe modes of embodiment of the present invention, referring to the attached drawings. It is to be noted that, in all of the drawings, any similar constituents will be given with same reference numerals, and not be represented the explanations therefor for simplicity.

First Embodiment

This embodiment relates to a particle manipulation unit manipulating flow of particles contained in a sample liquid, and guiding them to predetermined directions, with the aid of obstacles formed in a channel. FIG. 1 is a perspective view showing an exemplary configuration of a particle manipulation unit of this embodiment. As shown in FIG. 1, the configuration is such that a channel 1 formed on a substrate 41 is branched into a channel 2 and a channel 3 at a branching point 43, and that an obstacle portion, in which a plurality of columnar obstacles 8 are arranged as being spaced by regular gaps, is disposed at the branching point of the channel 1, channel 2 and channel 3.

First, a suspension containing the particles 4 is filled on the upstream side of the channel 1. Size of the particles 4 may typically be of the order of millimeter or smaller. It may still further be of the order of micrometer or smaller. The suspension respectively flows in the direction indicated by arrow 5 in the channel 1, in the direction indicated by arrow 6 in the channel 2, and in the direction indicated by arrow 7 in the channel 3. It is allowable herein to dispose a pump as an external force imposing unit allowing the suspension to flow, typically on the upstream side of the channel 1, or on the downstream sides of the channel 2 and channel 3. It is also allowable to make use of capillary phenomenon. Making use of capillary phenomenon is successful in getting rid of the external force imposing unit such as the pump, and in downsizing and simplifying the device as a whole.

Types of the unit are not limited so far as they are mechanisms capable of inducing flow of the suspension. The flow of the suspension also acts on the particles 4 so as to make them flow. It is also allowable to make only the particles 4 flow, without liquid flow, by electrophoresis or dielectrophoresis. For example, application of voltage between the individual electrodes, preliminarily provided to the channel 1, channel 2 and channel 3 (not shown), in successful in efficiently guiding the particles towards the electrodes, if the particles 4 have electric charges.

Figure 2:
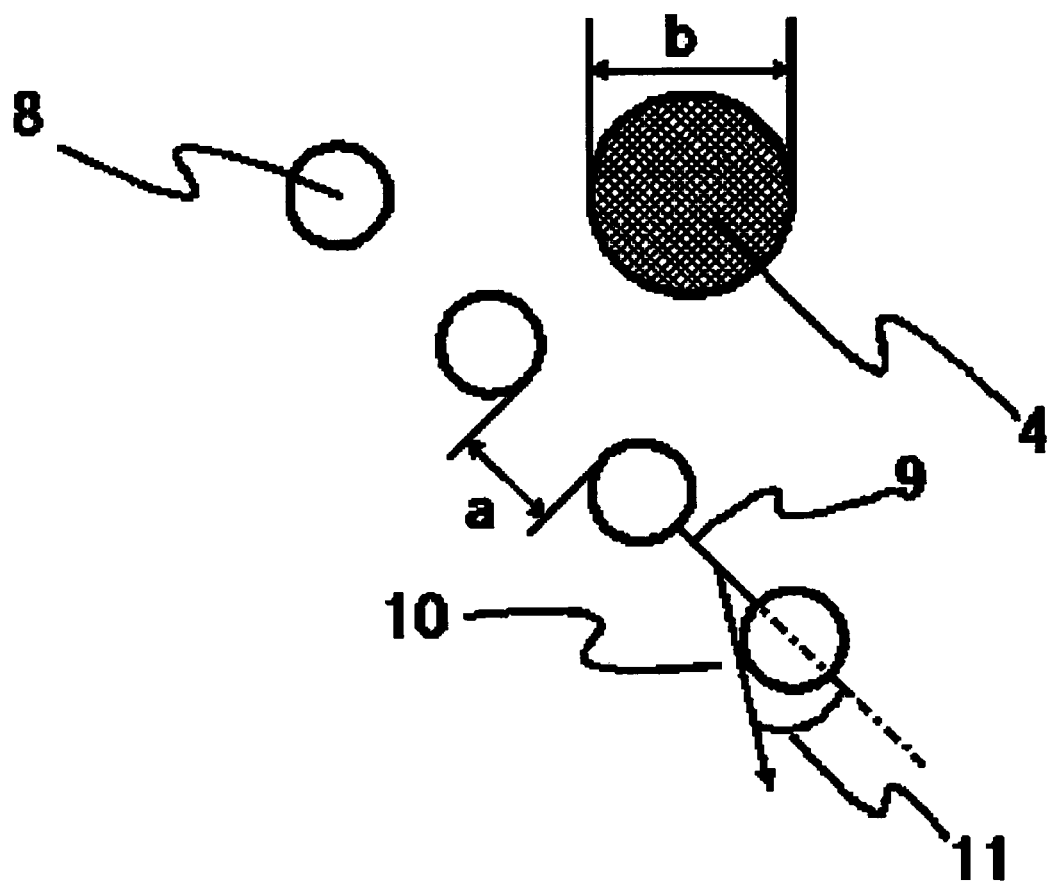
FIG. 2 is a top view showing obstacles disposed at a branching point of the particle manipulation unit shown in FIG. 1, and a particle present on the upstream side of the branching point.

At the branching point 43 in the particle manipulation unit shown in FIG. 1, only components, out of those contained in the suspension, capable of passing through the gap of the obstacles 8 flow into the channel 2, and the components incapable of passing therethrough flow into the channel 3. FIG. 2 is a top view showing the obstacles 8 disposed at the branching point and particles 4 present in the upstream side of the branching point 43. Next paragraphs will describe a mechanism of manipulating direction of flow of the particles 4 by the obstacle. It is to be noted that particle size taking deformation liability into consideration will be referred to as "effective particle size" in this patent specification.

When width "a" of the gap between a plurality of obstacles 8 is smaller than the effective particle size "b" of the particles 4 in consideration of the deformation liability in the solvent as shown in FIG. 2, probability of passage of the particles 4 towards the channel 2 will be smaller than probability of passage of the particles 4 towards the channel 3, due to resistance exerted on the particles 4 which are going to pass through the gaps. In this configuration, a line segment connecting the adjacent obstacles 8, which is a line segment 9 for example, is arranged as being inclined by a certain angle from a direction of force 10 exerted on the particles 4. In other words, with respect to an angle 11, a relation of 0°<angle 11<90° holds. This is because an angle 11 of 0° will make the whole portion of the suspension flow only into the channel 3, without causing components flowing into the channel 2. This is also because an angle 11 of 90° will prevent the particles 4 from flowing into the channel 3, causing clogging in the gaps between the obstacle 8 and deposition in the vicinity of the obstacles 8.

The direction of force 10 expresses direction of resultant force of forces expressed by arrows 5, 6 and 7. The particles 4 satisfying 0°<angle 11<90° never clog in the gaps between the obstacles 8, but gradually flow towards the direction of channel 3 in an average view, since they are under Brownian motion in the liquid.

For an exemplary case where the suspension is blood and the particles 4 are erythrocytes, width "a" of the gaps between a plurality of obstacle 8 may be adjusted to 3 μm or around. When the blood, as the suspension, is allowed to flow from the upstream side of the channel 1 with the aid of capillary phenomenon in this configuration, the erythrocytes at the branching point 43 flow together with the plasma toward the direction of channel 3, and only the plasma flows into the channel 2. This is successful in separating the plasma from blood without using a centrifuge.

This process using no buffer or the like for extraction causes no variation in the plasma concentration. In view of avoiding destruction of the erythrocytes, the angle 11 is preferably set to as small as possible, because it is desirable to minimize the resistance caused by the obstacles 8. Force exerted on the erythrocytes also relates to force of blood flow driven by capillary phenomenon, so that it is preferable to consider ratio of sectional areas of the channel 2 and channel 3, and it is preferable to make the sectional area of the channel 3 relatively larger in view of avoiding destruction of the erythrocytes.

As described in the above, the present embodiment is successful in configuring a unit manipulating flow in the channel 1 filled with a liquid, while allowing the particles 4 to flow therethrough. It is allowable to continuously flow the particles 4 in this manipulation of flow. This makes it possible to continuously process a relatively large amount of sample.

In the conventional manipulation of flow of particles having a particle size of 50 nm or smaller according, for example, to the method described in the aforementioned Non-Patent Document 1, there was a high level of accuracy required for the geometry of the obstacles 8, and fabrication of those having a complicated geometry was difficult even with micro-fabrication technologies. In contrast to this, the flow of the particles 4 in this embodiment is controlled by the gaps between a plurality of obstacles 8, and is hardly affected by the geometry of the obstacles 8. This successfully prevents a requirement on the geometrical accuracy of the obstacles 8 from going into an order smaller than that of the particle size. In other words, it is made possible to control the flow of the particles 4 with a high level of accuracy even by adopting a columnar structure having a circular section which can readily be fabricated by the general procedures of micro-fabrication. Therefore the particle manipulation unit of this embodiment can readily be fabricated, and is capable of continuously manipulating the flow of the particles 4.

Silicon is used as a material composing the substrate 41. It is preferable to form a silicon oxide film on the surface of silicon. The silicon oxide film provides hydrophilicity to the surface of the substrate 41, and makes it possible to successfully form a sample channel. It is also allowable to use glasses such as quartz, or plastic materials. Examples of the plastic materials include silicone resin, thermoplastic resins such as PMMA (polymethyl methacrylate), PET (polyethylene terephthalate) and PC (polycarbonate), and thermosetting resins such as epoxy resin. These materials, characterized by their simplicity in molding and processing, are successful in suppressing the production cost. Metals may be used for the substrate 41.

The obstacles 8 can be formed by etching the substrate 41 so as to have a predetermined pattern, wherein methods of fabrication is not specifically limited.

Although the obstacles 8 shown in FIG. 1 are circular cylinders, they are not limited to circular cylinders or pseudo-cylinders such as elliptic cylinders, and even may be: cones including circular cone and elliptic cone; prisms including triangular prism and quadrangular prism; and prisms having other sectional shapes. It is to be noted that prisms are more preferable than cones in view of precisely controlling the flow of the particles.

It is also allowable to form, in place of the obstacles 8, a plate-formed partition wall having a plurality of openings. Geometry of the openings formed herein in the partition wall may appropriately be selected from circle, oval or polygonal hole or slit, depending on geometry and size of the particles 4.

Size of the obstacles 8 may be such as 10 nm to 10 μm or around in width. The gap between the adjacent obstacles 8 is typically adjusted to 5 nm to 10 μm, which may appropriately be selected depending on size and geometry of the particles 4. The height illustrated in FIG. 1 is set almost equivalent to the depth of the channel 1.

It is also allowable to form a cover on the surface of the substrate 41. Provision of the cover suppresses drying or the like of the sample liquid in the channel 1, channel 2 and channel 3. Materials for composing the cover may be selected typically from those used for the substrate 41. Both of materials same with, or different from those for the substrate 41 may be allowable.

Next paragraphs will describe a method of fabricating the particle manipulation unit shown in FIG. 1. The channel 1, channel 2, channel 3 and obstacles 8 can be formed on the substrate 41 typically by etching the substrate 41 so as to have a predetermined pattern, wherein the method of fabrication is not specifically limited.

For example, fabrication with the aid of electron beam exposure technique using calixarene, a kind of resist for micro-fabrication, is adoptable. An example of molecular structure of calixarene is shown below. calixarene is used as a negative resist for electron beam exposure, and is suitable for micro-fabrication of a nanometer scale.

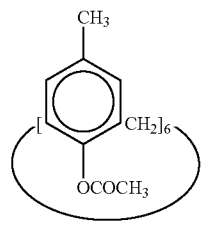

A silicon substrate having a surface orientation of (100) is used herein as the substrate 41. First, a silicon oxide film and a calixarene electron beam negative resist film are formed in this order on the substrate 41. Thicknesses of the silicon oxide film and calixarene electron beam negative resist film are adjusted to 40 nm and 55 nm, respectively. Next, regions for forming the obstacles 8 are subjected to electron beam exposure using an electron beam exposure apparatus. The resist is developed using xylene, and rinsed with isopropyl alcohol. This process results in patterning of the calixarene negative resist for electron beam exposure.

Next, a positive photoresist is coated over the entire surface. The thickness is set to 1.8 μm. The calixarene resist remained after the electron beam exposure and development does not dissolve into a solvent of the positive photoresist. The photoresist is then subjected to light exposure through a mask so as to expose regions for forming the channel 1, channel 2 and channel 3, and is developed. These processes result in formation of a resist mask composed of calixarene and positive photoresist.

Next, the silicon oxide film is dry-etched through the resist mask, using a mixed gas of $CF_4$ and $CHF_3$. The remained positive photoresist is removed by organic washing using a mixed solution of acetone, alcohol and water, and still remained positive photoresist and calixarene resist are removed by oxidative plasma treatment. Next, using the silicon oxide film having the resist pattern transferred thereon as a mask, the silicon substrate is dry-etched to a depth of 2 μm, using an HBr gas. Next, the silicon oxide film is removed by wet etching using a buffered aqueous hydrofluoric acid solution. These processes result in formation of the channel 1, channel 2, channel 3, and obstacles 8 on the substrate 41.

Succeeding to the aforementioned process steps, it is preferable herein to further convert the surface of the substrate 41 into hydrophilic. Hydrophylic conversion of the surface of the substrate 41 is successful in smoothly introducing the sample liquid into the channel 1, channel 2, channel 3 and obstacles 8. In particular at the branching point 43 where the channel is micronized due to the obstacles 8, the hydrophilic conversion of the surface of the individual channel successfully promotes introduction of the sample liquid with the aid of capillary phenomenon, and improves accuracy in the manipulation of flow.

For this reason, the substrate 41 after the etching process is placed in an oxidation furnace, to thereby form a thermal oxide film of silicon. Conditions for annealing herein are selected so as to form the silicon thermal oxide film to as thick as 30 nm. In this case, array of the obstacles 8 is designed preliminarily considering the thickness of the oxide film. Formation of the silicon thermal oxide film successfully clears difficulty in introducing the liquid into a separation device. For the case where the cover is thereafter provided, anodic bonding is carried out for sealing, to thereby complete the particle manipulation unit.

For the case where any plastic material is used for the substrate 41, it is allowable to adopt any publicly-known method suitable for material composing the substrate 41, such as etching, press forming using die such as embossing, injection molding, and forming based on photo-curing.

Also for the case where plastic materials are used for the substrate 41, it is preferable to convert the surface of the substrate 41 into hydrophilic. The hydrophilic conversion of the surface of the substrate 41 makes it possible to smoothly introduce the sample liquid into the region where the channels and obstacles 8 are formed. In particular at the branching point 43 where the channel is micronized due to the obstacles 8, the hydrophilic conversion of the surface of the substrate 41 successfully promotes introduction of the sample liquid with the aid of capillary phenomenon.

As one exemplary surface treatment for imparting hydrophilicity, it is allowable to coat a coupling agent having a hydrophilic group on the side wall of the channels. The coupling agent having a hydrophilic group can be exemplified by silane coupling agents having amino group, and specific examples of which include N-β(aminoethyl)γ-aminopropylmethyldimethoxysilane, N-β(aminoethyl)γ-aminopropyltrimethoxysilane, N-β(aminoethyl)γ-aminopropyltriethoxysilane, γ-aminopropyltrimethoxysilane, γ-aminopropyltriethoxysilane, and N-phenyl-γ-aminopropyltrimethoxysilane. These coupling agents can be coated by spin coating, spraying, dipping, vapor phase process and so forth.

The particle manipulation unit shown in FIG. 1 was configured as having the first channel which comprises the channel 1 and channel 2, and the second channel which comprises the channel 3 branched out from the first channel at the branching point 43. Directions of formation of the channel 1 and channel 2 in FIG. 1 coincide with each other, and the channel 3 inclines at a certain angle to the channel 1 and channel 2, whereas it is also allowable that the channel 1 and channel 2 may form a predetermined angle therebetween.

Second Embodiment

Figure 3:
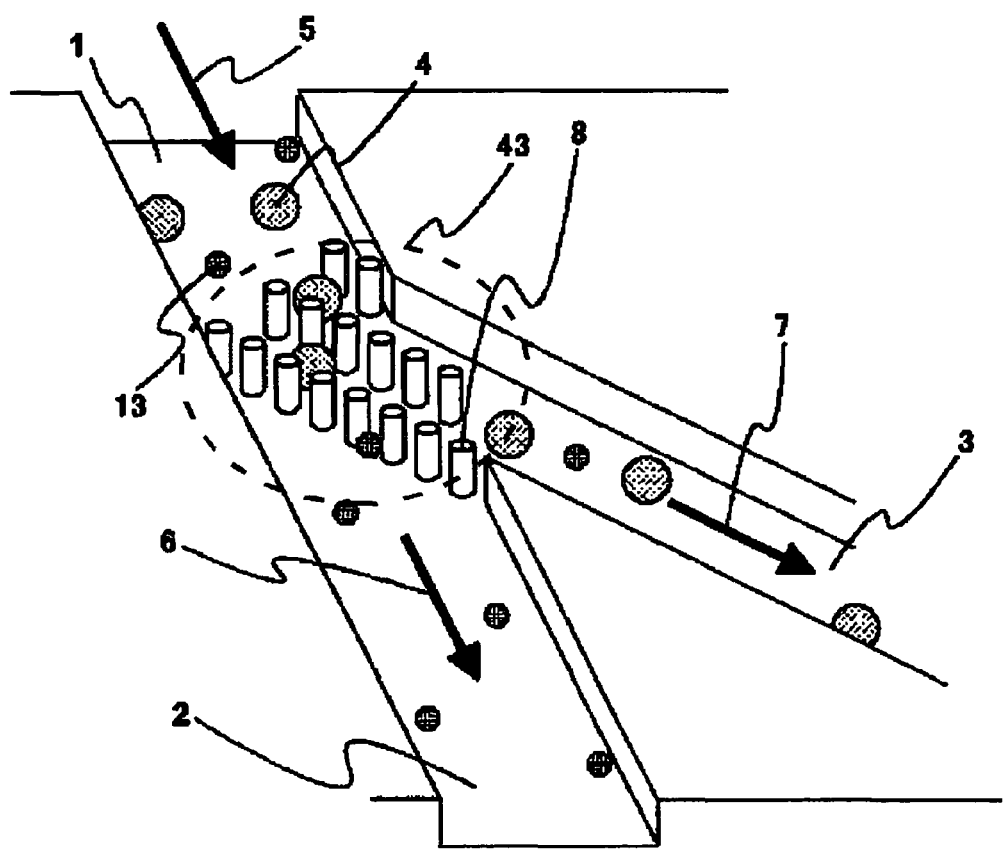
FIG. 3 is a perspective view showing an exemplary configuration of a particle manipulation unit of the present embodiment.

This embodiment relates to a particle manipulation unit manipulating flow of particles contained in a sample liquid, and guiding them to predetermined directions, with the aid of obstacles formed in a channel. This embodiment differs from the first embodiment in having a region in which multiple stages of obstacle portions are formed. FIG. 3 is a perspective view showing an exemplary configuration of a particle manipulation unit of this embodiment.

Figure 4:
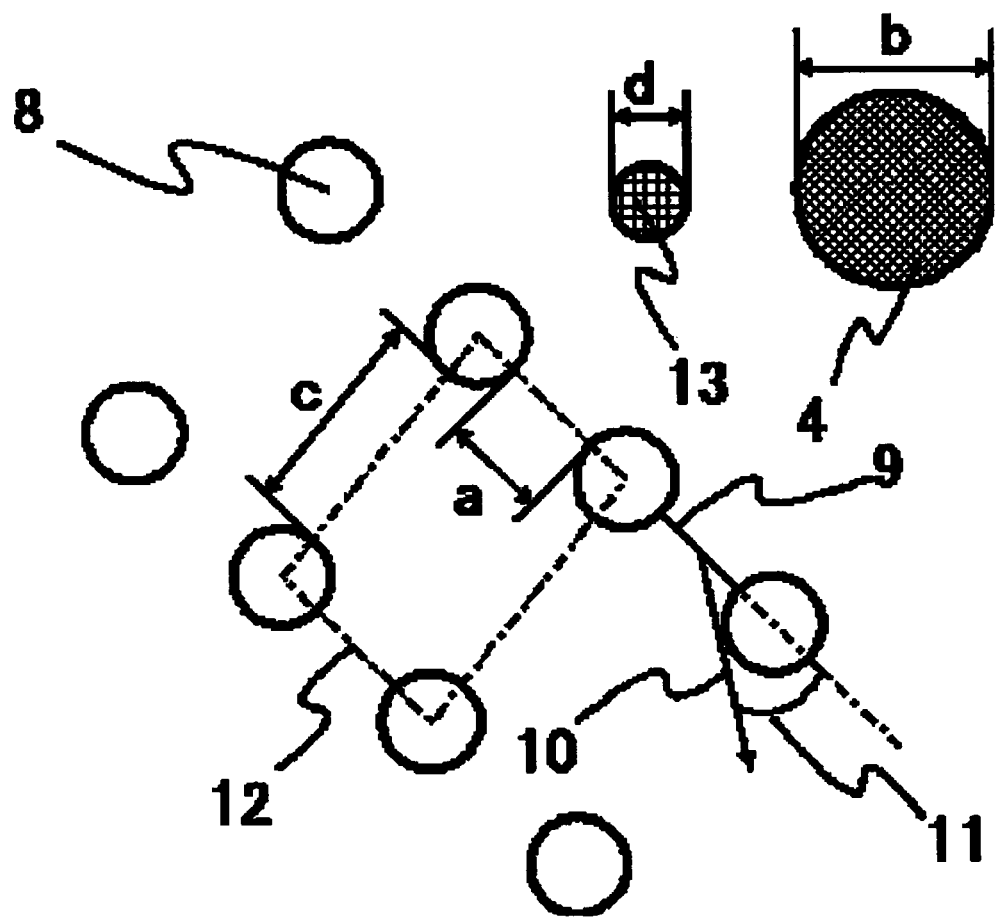
FIG. 4 is a top view showing obstacles disposed at a branching point of the particle manipulation unit shown in FIG. 3, and a particle present on the upstream side of the branching point.

FIG. 4 is a top view showing the obstacles 8 disposed at the branching point 43, and particles present in the upstream side of the branching point 43. Next paragraphs will describe a mechanism of manipulating direction of flow of the particles 4 by the obstacle. As shown in FIG. 4, the structure of arrangement of multiple stage of obstacles 8 has a unit cell 12 indicated by a dashed line formed therein. As for width of gaps in the unit cell 12, as shown in FIG. 4, width "a" of the gap is set smaller, and width "c" of the gap is set larger, as compared with effective particle size "b" of the particles 4 in consideration of the deformation liability in the sample liquid. In short, a relation of a<b<c holds. The particles 4 are therefore going to flow in direction 10 under the resultant force, but can migrate only with a small probability through the array of the obstacles 8 in a direction crossing width "a" because width "a" is small, and instead most portion of which will flow towards the channel 3, while repeating collision with the obstacles 8 caused by Brownian motion.

In this embodiment, there is a portion where multiple stages of the array structure of the obstacles 8 are provided in the direction of resultant force 10. For the particles 4 capable of deforming themselves to a certain degree, including biological polymers such as DNA and protein, provision of the multiple stages of the array structure can further reduce the probability of migration through the obstacles 8 in a direction crossing width "a". It is to be noted that the particles to be manipulated in the flow by the particle manipulation unit of this embodiment are not limited to biological molecules, and any of those composed of polymer resin, metal or semiconductor, such as antibody-immobilized polystyrene beads or gold particles, and semiconductor quantum dots are applicable, allowing continuous manipulation of flow of the particles.

The sample liquid to be manipulated in this embodiment may contain further smaller particles 13 besides the particles 4, as shown in the drawing. Effective particle size "d" of the particle 13 in the sample liquid is smaller than width "a" of the gap between the obstacles 8. In short, a relation of d<a<b<c holds. The particle 13 therefore has a sufficiently large probability of migration through the array of the obstacles 8 in a direction crossing width "a". By allowing a suspension containing the particles 4 and particles 13, as the sample liquid, to flow from the upstream side of the channel 1, it is made possible to extract the liquid containing no particle 4 in the channel 2.

The particle manipulation unit of this embodiment is therefore said to have a function of two-dimensionally separating the particles 4 and particles 13, depending on their sizes. Although the particles 13 flow also into the channel 3 in this embodiment, it is also possible to suppress amount of the particles 13 flowing into the channel 3 to a sufficiently small level, by proper adjustment of force causative of the particle flow, and by appropriate design of structure of the branching point.

Figure 11:
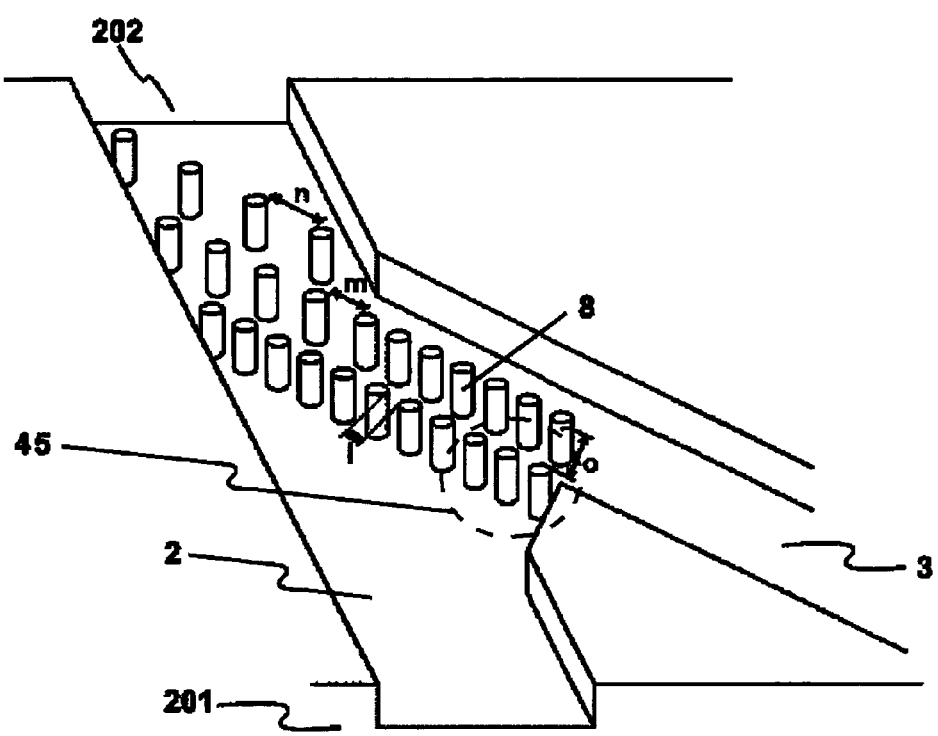
FIG. 11 is a perspective view showing an exemplary configuration of obstacles disposed at a branching point of a particle manipulation unit of the present embodiment.

FIG. 11 is a perspective view showing a configuration of the obstacles disposed at the branching point of the particle manipulation unit of this embodiment. In this configuration of the particle manipulation unit shown in FIG. 11, which will be described later, an angle portion at the intersection portion of the channel 2 and channel 3 is notched off, to thereby form a channel expanded portion 45. Formation of the obstacles 8 also in the channel expanded portion 45 makes it possible to increase length of the array of the obstacles 8, and to thereby manipulate the flow of the particles in more accurate and efficient manner.

Materials and methods of fabricating the particle manipulation unit of this embodiment may be the materials and methods described for example in the first embodiment. The particle manipulation unit of this embodiment has multiple stages of obstacles 8 formed therein, wherein the geometry of the obstacles per se can readily be fabricated using microfabrication technologies, configured as making it possible to more accurately control the particle flow.

Third Embodiment

Figure 5:
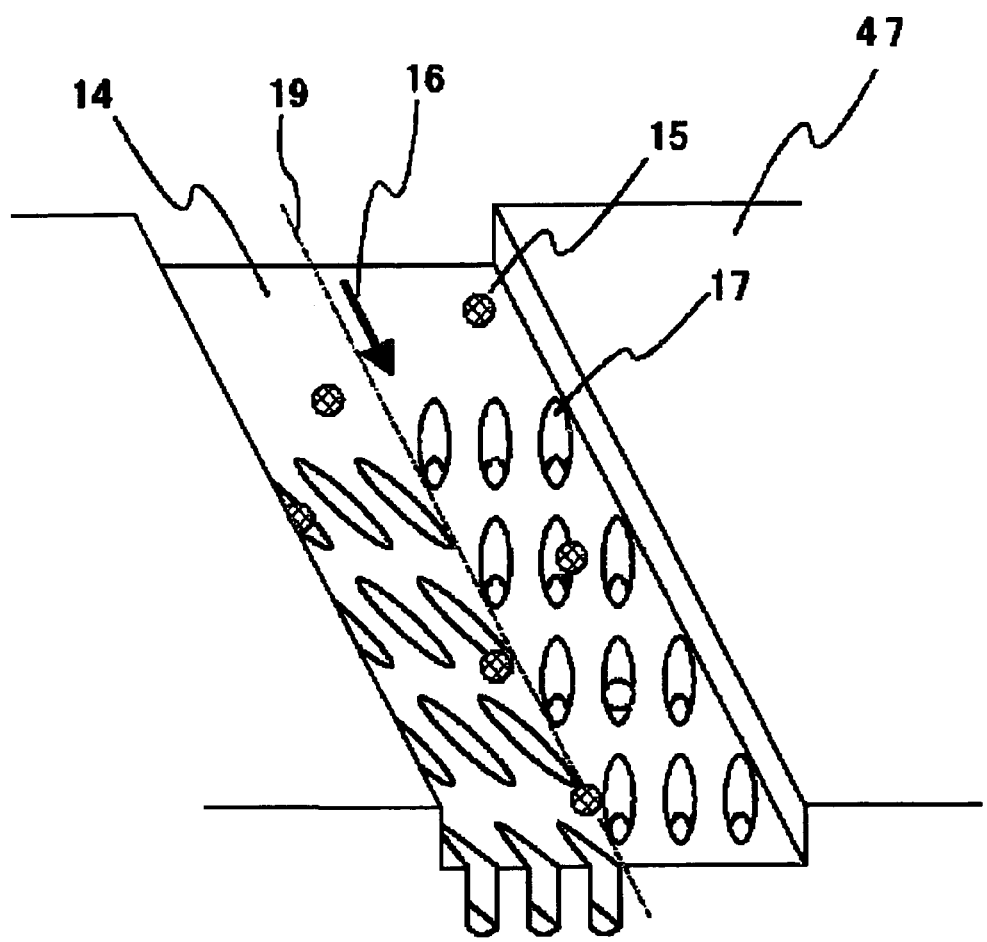
FIG. 5 is a perspective view showing an exemplary configuration of a particle manipulation unit of the present embodiment.

This embodiment relates to a unit manipulating the particle flow, having an array structure of the obstacles configured by unit cells, each of which having a trench structure formed on the wall surface of the channel, capable of interacting with particles of a predetermined size. FIG. 5 is a perspective view showing an exemplary particle manipulation unit of this embodiment. As shown in FIG. 5, a channel 14 is formed on a substrate 47. The sample liquid, having particles 15 suspended therein, is filled on the upstream side of the channel 14. The particles 15 flow in the direction indicated by an arrow 16 in FIG. 5. Similarly to the first embodiment, force making the particles 15 flow in the direction of arrow 16 may be generated by a method such as electrophoresis, dielectrophoresis or the like, or by any other forces exerted on the particles 15.

Figure 6:
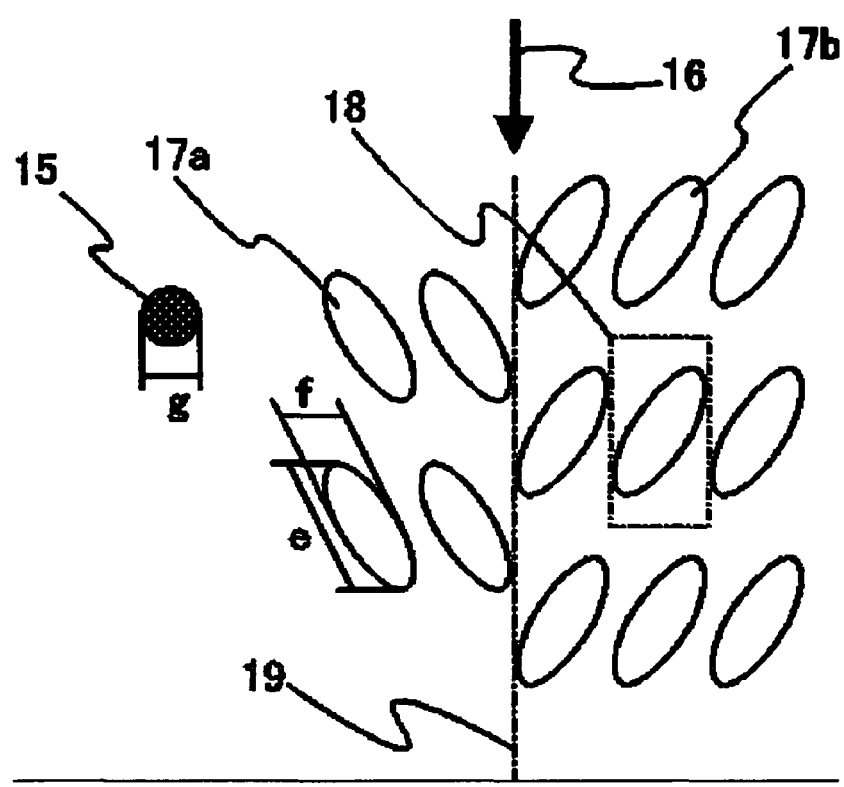
FIG. 6 is a top view showing obstacles disposed at a branching point of the particle manipulation unit shown in FIG. 5, and a particle.

As shown FIG. 5, the channel 14 has an array structure, in which a trench structure 17 configures a unit cell, formed on the bottom surface of the channel. The trench structure 17, although being formed on the bottom surface of the channel 14 in this embodiment, may be formed on other wall surfaces. FIG. 6 is a top view showing a part of the array structure composed of the trench structure 17. As shown in FIG. 6, the array structure is formed by unit cells composed of the trench structure 17 as surrounded by a dashed line 18. The array structure includes two types of array structures, which are trench structures 17a and trench structures 17b in a mirror symmetry therewith, as being bounded by a dashed line 19.

This sort of trench structure can be fabricated by semiconductor micro-fabrication technologies or MEMS technologies. For an exemplary case where the flow of the particles having a particle size of 50 nm or smaller, such as protein, is manipulated, the trench structure may be fabricated also using a porous material which can be formed in a self-organizing manner. Mesoporous structure, which is owned by silica, zirconia and so forth, is well-known porous material, and the array structure of which can be formed using an organic polymer film as a template. Anodization of an aluminum film is successful in forming an array structure of the trench structure composed of anodized alumina in a self-organizing manner, wherein it is still also possible to fabricate the ordered structure shown in FIG. 6, by preliminarily forming scratches, which serve as nucleation points, on the aluminum film by the nano-imprinting process or the like prior to the anodization, and then by anodizing the aluminum film.

The particle manipulation unit shown in FIG. 5 shows differences both in diameter of the trench structure 17 provided to the bottom surface of the channel 14, and in periodicity of the unit cells differ by directions in a two-dimensional plane, wherein the difference may be shown only in either one of them. The trench structure 17 shown in FIG. 5 typically has an elliptic geometry, while not being limited to the elliptic geometry. Long diameter "e" and short diameter "f" of elliptic pits provided to the bottom surface of the channel 14 are preferably close to particle size "g" of the particles 15 in view of ensuring thorough interaction therebetween. The trench structure 17 having such elliptic geometry with different diameters in the two-dimensional plane raises difference also in the interaction with the particles 15 in a two-dimensional plane ascribable to the difference. If the periodicity of the trench structure 17 differs in the two-dimensional plane, frequency of interaction given by the trench structure 17 to the particles 15 during their flow will differ by directions in the two-dimensional plane.

As described in the above, a particle manipulation unit manipulating flow of the particles 15 can be realized also by making the obstacles as the trench structure 17. The trench structure 17 herein raises resistance against the flow of the particles 15, and magnitude of the resistance depends on size of the particles 15. It is therefore made possible to provide specific treatment such as separation, condensation and so forth to specific particles in the sample, based on a fact that magnitude of interaction between the trench structure 17 and particles 15 differs depending on geometry and size of the particles 15.

It is to be noted that the interaction originating the manipulation of the particles 15 is generally weak as compared with the interactions ascribable to the arrangement of the columnar obstacles shown in the first or second embodiment, so that the trench structure 17 is preferably provided to form multiple stages along the direction of flow of the particles 15. The array structure shown in FIG. 5 is such that the long axis and short axis of the trench structure 17 are oriented neither in parallel with, nor normal to force causing flow of the particles 15 indicated by the arrow 16. This makes it possible to efficiently manipulate the flow of the particles 15 within the channel 14 leftward or rightward in the drawing.

In this embodiment, the mirror symmetry of the array structure allows the particles 15 to gather in the vicinity of the dashed line 19 indicating the boundary. This successfully provides a condensation effect of the particles 15. The dashed line 19 and the arrow 16 are aligned in parallel in this embodiment, whereas it is also allowable to form a non-parallel trench structure. Arrangement of the trench structure is not limited to the mirror symmetric one, but it is allowable to select any desired arrangement corresponding to configurations such as having, or not having branching of the channel 14.

Provision of a straight passageway and a channel branching therefrom on the downstream side of the particle manipulation unit of this embodiment will make it possible, for example when a dispersion having a single kind of particles dispersed therein is allowed to flow therethrough, to direct the separated and condensed particles to the straight channel, and to recover the dispersion solvent from the branched channel.

Fourth Embodiment

Figure 7:
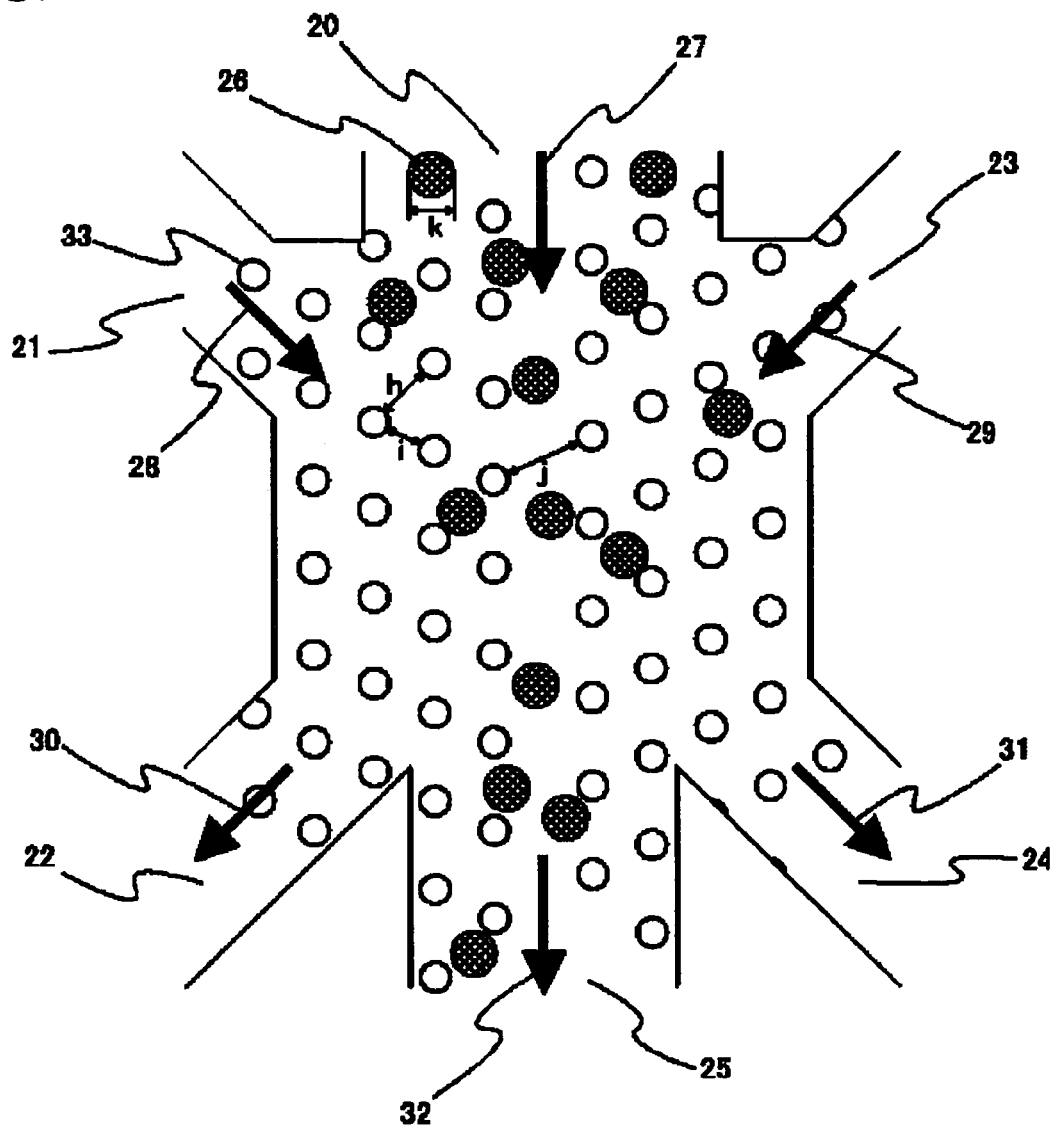
FIG. 7 is a top view showing an exemplary configuration of a particle manipulation unit of the present embodiment.

A particle manipulation unit of this embodiment has the obstacles arranged in a two-dimensional manner, used for dilution, desalting, solvent replacement and so forth of the sample liquid. FIG. 7 is a top view showing a particle manipulation unit of this embodiment, manipulating the particle flow. In the particle manipulation unit shown in FIG. 7, a channel 20 formed on a substrate (not shown) has a channel 21 and a channel 23 connected thereto, and has a branching points on the downstream side of the connection points, from which three channels, that are a channel 22, a channel 24, and a channel 25 are branched out. The obstacles are formed at the branching point, and on the upstream side of the branching point. In short, the obstacles in FIG. 7 are formed over a region ranging from the vicinity of the connection point of the channels to the branching point.

Considering now that the channel 20 is assumed as a channel allowing a sample suspension containing particles 26, or a buffer, to flow therethrough towards the branching point, and that the channel 21 and channel 23 are assumed as the channels allowing a buffer solution for dilution, a washing solution for desalting, or a solvent for replacement to be introduced therethrough towards the branching point. The channels 22 and 24 are channels extracting the waste liquid from the branching point. The channel 25 is the one extracting a liquid containing the particles 26 after the dilution, desalting or replacement. Arrows 27 to 32 given in the connection points of the individual channels to the branching point indicate directions of the liquid at the connection region of the channels. In the region corresponded to the branching point, a plurality of columnar obstacles 33, spaced by a gap from each other, are arranged with a mirror symmetry, as shown in FIG. 7.

Widths "h", "i" and "j" of the gap between a plurality of obstacles 33, in comparison with particle size "k" of the particle satisfy a relation of j>h>k>i. The particles 26 are therefore hard to pass through the array of the obstacles 33 in a direction crossing width "i", and easy to pass in directions crossing widths "h" and "j". This makes the particles 26 more likely to be guided and allowed to pass from the channel 20 to the channel 25 in a selective manner, and more unlikely to flow into the channel 22 and channel 24, resulting in selective discharge into the channel 25.

On the other hand, the buffer for dilution, washing solution for desalting, or solvent for replacement are sufficiently small in the molecular size, can be mixed at the branching point irrespective of the width of the gap between the obstacles 33, and are discharged out from the channel 22, channel 24, and channel 25. Use of the particle manipulation unit shown in FIG. 7 can therefore realize a function of diluting the liquid, desalting the buffer, or replacing the solvent.

Materials and methods of fabricating the particle manipulation unit of this embodiment may be the materials and methods described for example in the first embodiment.

Each of the particle manipulation unit respectively realizing a function of separation, condensation, dilution, solvent replacement and so forth shown in the above-described modes of embodiment can be used in a singular manner, or in combination. For the combined use, the units can be fabricated with a low cost by integrating them on a single substrate. A continuous execution of desired treatment on a chip based on integration on a single substrate is, therefore, successful in suppressing loss of sample between the individual units, as compared with the case where the individual units are independently used.

This advantage in the particle manipulation unit stays effective power also in the case where such chips are mounted on an analyzer, detector and so forth for sample components, to thereby configure a particle treatment system. For the case where the particle is protein, this sort of particle treatment system can be exemplified by an analyzer such as protein analyzing system coupled with a mass spectroscope, but allows various configuration without being limited to this example.

Fifth Embodiment

Figure 8:
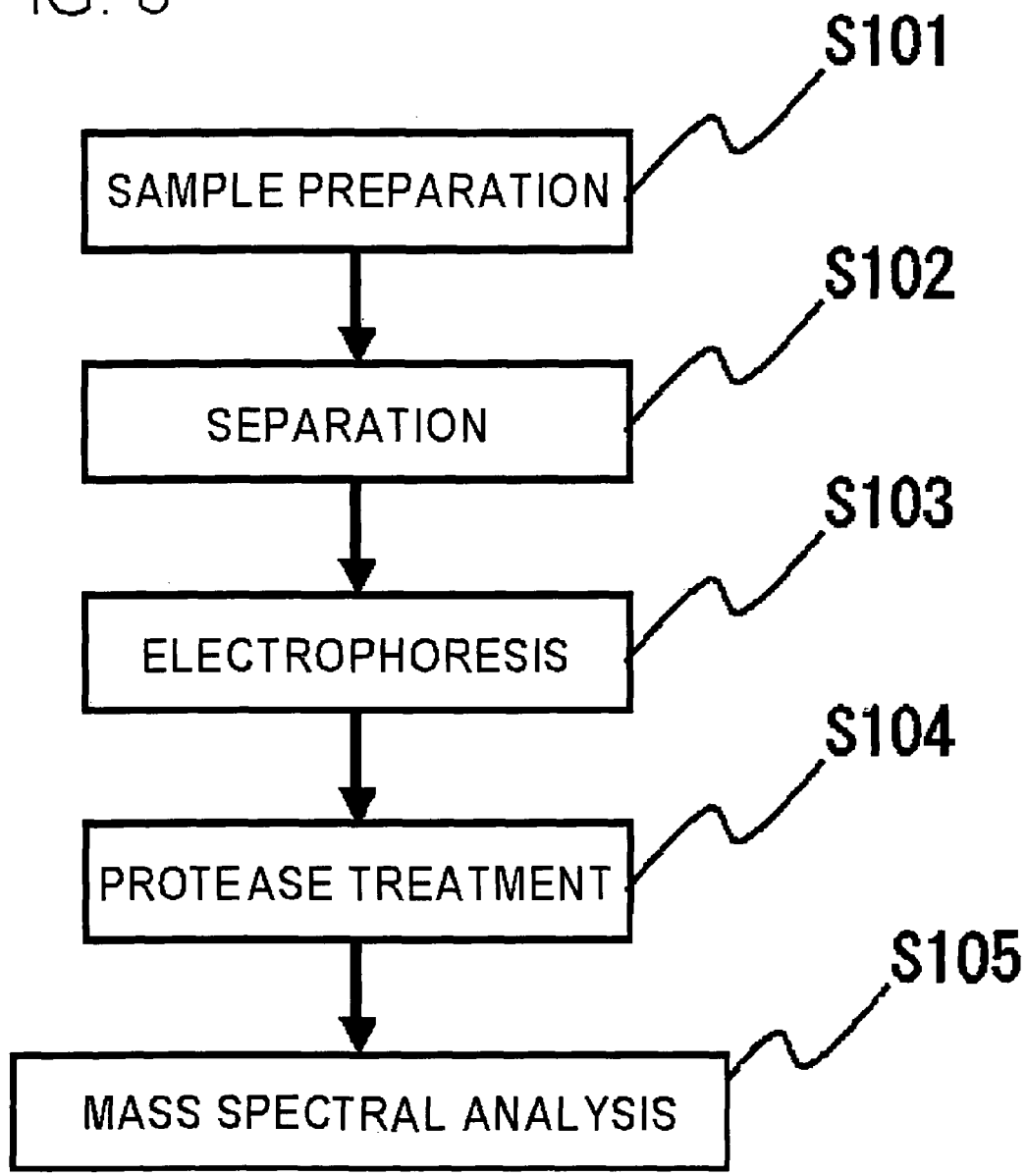
FIG. 8 is a chart showing analytical procedures of proteins of the present embodiment.

This embodiment relates to a particle treatment system separating and identifying a specific protein contained in a sample. FIG. 8 shows a chart showing procedures for analyzing protein according to this embodiment.

Step 101 shows a sample preparation step extracting a protein to be analyzed from cells, tissues or biological specimens, and treating the extract solution to provide a sample form suitable for electrophoresis.

Step 102 is a step of separating the protein to be analyzed according to its size, using a chip having the particle manipulation unit described in the second embodiment. A chip shown in FIG. 10, for example, can be used as the chip of this kind. The chip shown in FIG. 10 will be detailed later.

Step 103 is a step of separating the protein by electrophoresis, and typically includes two-dimensional electrophoresis separating proteins depending on their isoelectric points and molecular weights, and chromatographic separation as a pretreatment therefor.

Step 104 is a protease treatment step, in which the protein is hydrolyzed by a protease to obtain a decomposed product containing peptides.

Step 105 is a step of subjecting the decomposed product obtained in step 104 to mass spectral analysis to determine molecular weights of the peptides, to thereby identify a species of the protein. Step 105 also includes process steps such as pretreatment including desalting required prior to the mass analysis, and posttreatment including determination of amino acid sequence or amino acid composition.

The conventional method having no step 102 of separation using the particle manipulation unit has been suffered from problems below. Two-dimensional electrophoresis is extremely high in the resolution power, but allows only a small amount of protein chargeable into a gel for the two-dimensional electrophoresis. Because the populations of proteins are not constant depending on the species, and presence of any large population of protein makes minor proteins with a small population appear only in a small content in spots obtained after the two-dimensional electrophoresis. The spots could not therefore be recognized due to scarceness of the protein, and were hard to recover. Even if it should be possible to recognize the spots, it has been usual for the protein to go under the detection limit of mass analysis due to its scarceness, and could not have been detected.

In contrast, this embodiment involves, in step 102, separation prior to the electrophoresis. In this step, proteins with large populations are separated and excluded depending on their sizes, using the particle manipulation unit shown in FIG. 3, having the separation function described in the second embodiment. This successfully solves the above-described problems with respect to the conventional problems, and makes it possible to analyze proteins with small populations. Because amount of charge of the minor proteins into the gel can be increased by the preliminarily rough separation of the proteins by sizes, without carrying out separation and exclusion targeted at the proteins with large populations, it is also made possible to relieve the problem of sample shortage. Use of the particle manipulation unit shown in FIG. 3 herein allows continuous separation, and this is advantageous in readily ensuring a necessary amount of charge of proteins to be charged on the gel in the two-dimensional electrophoresis. This is also advantageous in that the particle manipulation unit, fabricated by the micro-fabrication technologies without using gel, is less degradable with time, and excellent in reproducibility of the separation.

Figure 10:
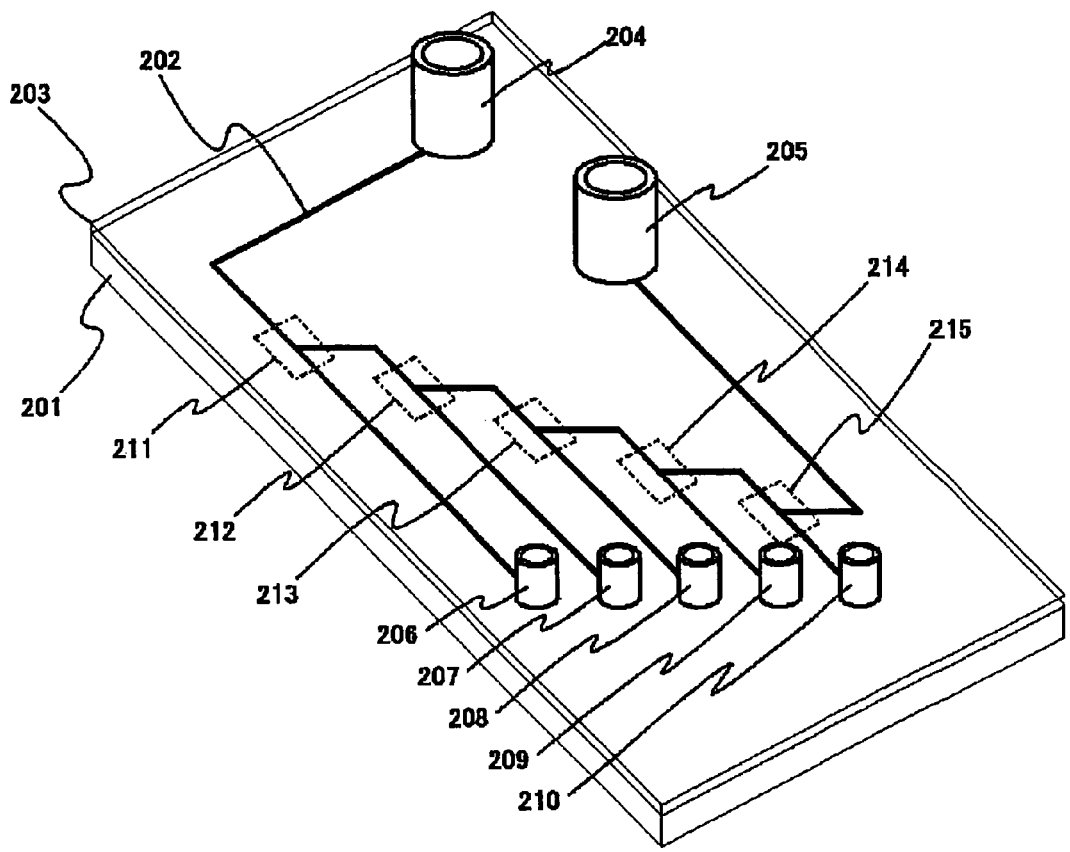
FIG. 10 is a drawing showing an exemplary configuration of a chip of the present embodiment.

It is also allowable to separate a sample, after being separated using the chip shown in FIG. 10 as described in the above, by two-dimensional electrophoresis, to further prepare it as a sample for MALDI-TOFMS (Matrix-Assisted Laser Desorption Ionization-Time of Flight Mass Spectrometer) for proteins, and to subject the sample to the measurement.

It is necessary for proteins to be measured by MALDI-TOFMS to be reduced in the molecular weight thereof to as small as 1000 Da or around, so that the proteins are reduced in the molecular weight thereof in step 104, mixed with a matrix solution, and then prepared as a dried sample.

For the case where the proteins to be measured have intramolecular disulfide bonds, the proteins are first subjected to a reduction reaction in a solvent such as acetonitrile containing a reducing agent such as DTT (dithiothreitol). The reduction reaction successfully allows the next decomposition reaction to proceed in an efficient manner. After the reduction, it is preferable herein to protect the thiol groups typically by alkylation, so as to prevent them from being oxidized again.

Next, the reduced protein molecules are digested using a protease such as trypsin. The digestion, which proceeds in a buffer solution such as phosphate buffer, is followed by desalting and removal of a high-molecular-weight fraction, or trypsin. The product is mixed with the matrix for MALDI-TOFMS.

The mixture is condensed and dried, so as to allow a mixture of the matrix and decomposed proteins to deposit. The dried sample is set to an MALDI-TOFMS apparatus, and mass analysis of step 105 carried out under application of voltage and irradiation of a nitrogen laser beam of 337 nm, for example.

Figure 14:
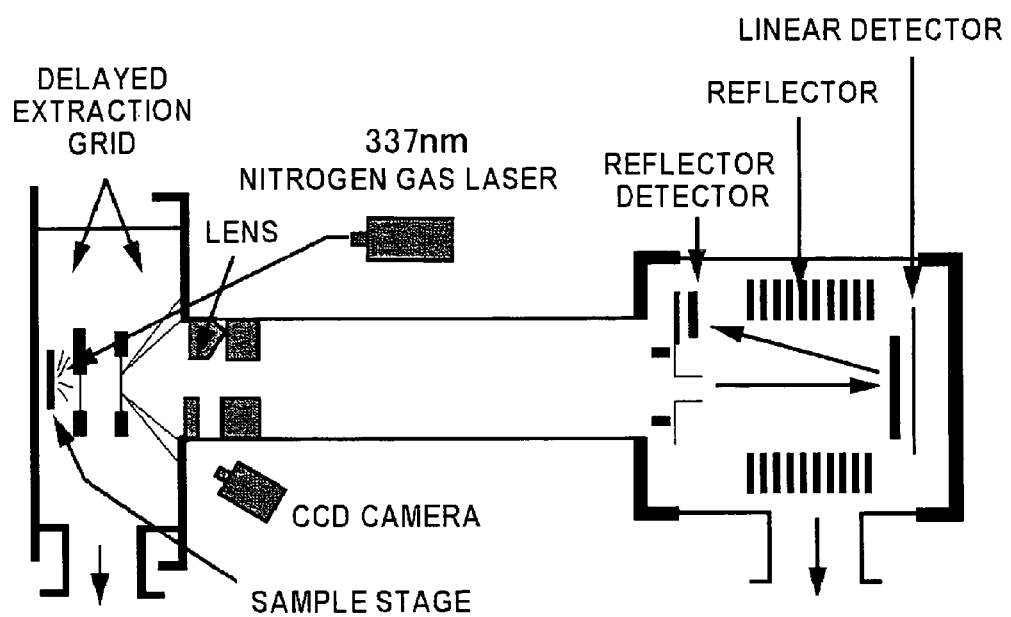
FIG. 14 is a drawing schematically showing a configuration of a mass spectroscope.

The mass spectroscope used in this embodiment will now be briefed. FIG. 14 is a schematic drawing showing a configuration of the mass spectroscope. On a sample stage shown in FIG. 14, the dried sample (not shown) obtained by the above-described procedures is placed. The dried sample is irradiated in vacuo with a nitrogen laser beam of 337 nm. The dried sample evaporates together with the matrix. The sample stage serves as an electrode, so that the evaporated sample flies in vacuum under the applied voltage, and is detected by a detection section which comprises a reflector detector, a reflector, and a linear detector.

It is therefore made possible to carry out MALDI-TOFMS, by placing the dried sample in a vacuum chamber of the MALDI-TOFMS apparatus.

The matrix for MALDI-TOFMS can appropriately be selected depending on target substance, and examples of which include sinapinic acid, α-CHCA(α-cyano-4-hydroxycinnamic acid), 2,5-DHB (2,5-dihydroxybenzoic acid), mixture of 2,5-DHB and DHBs (5-methoxysalicylic acid), HABA (2-(4-hydroxyphenylazo)benzoic acid), 3-HPA (3-hydroxypicolinic acid), dithranol, THAP (2,4,6-trihydroxyacetophenone), IAA (trans-3-indoleacrylic acid), picolinic acid, and nicotinic acid.

FIG. 10 is a drawing showing a configuration of a chip used in this embodiment. The chip shown in FIG. 10 has a function of separating proteins, ascribable to five particle manipulation units used for detecting proteins in this embodiment integrated on a single substrate. A channel 202 is formed on a silicon substrate 201, and a lid 203 is adhered thereon. Lithography using an electron beam exposure apparatus is carried out, since fabrication of the channel 202 and obstacles demands formation of narrow gaps on the silicon substrate 201. The fabrication can be accomplished by adopting a process in which the silicon substrate 201 is then dry-etched, and subjected to thermal oxidation so as to increase the diameter of the columnar obstacles, to thereby narrow the gaps. Method of fabricating such narrow gaps is not limited to the above-described one, but may be other fabrication process such as processing a glass substrate, and an aluminum thin film is formed thereon and oxidized.

The silicon substrate 201 which is excellent in applicability to micro-fabrication was employed in this embodiment, wherein the substrate is by no means limited to silicon, and may be any substrate composed of polymer resin, metal or insulating material. A glass was employed as a material of the lid 203 in this embodiment for the convenience of anodic bonding with the silicon substrate 201, wherein the method of adhesion is not limited to the anodic bonding, and polymer resin, metal, insulting material and so forth can be used as a material for the lid 203, not being limited to glass.

On the lid 203, there are provided seven liquid-feeding pipe ports 204, 205, 206, 207, 208, 209 and 210, which are respectively communicated with the channel 202, penetrating the lid 203. The channel 202 has five branching points 211, 212, 213, 214 and 215, surrounded by dashed lines.

Each of the branching points is configured as schematically shown in FIG. 11. More specifically, the multiple-stage arrangement of the columnar obstacles is configured in the channel, so as to provide the particle manipulation unit having a function of two-dimensionally separating proteins depending their sizes. A suspension liquid containing various sizes of proteins is fed from the liquid feeding pipe port 204 into the channel 202, allowed to flow through the branching points 211 to 215, and then discharged out from the liquid feeding pipe ports 205 to 210. Array of the obstacles at each of the branching points is such that, as shown in FIG. 11, the gap on the upstream side of the channel 202 has a larger width "n", and the gaps more further on the downstream side have more smaller widths "m" and "l". Width "o" of the gap is ensured as sufficiently wide.

In this design, proteins coming from the upstream side of the channel 202 readily enter the branching point, wherein any proteins, having sizes larger than width "l" and therefore cannot pass through the gaps having width "l" at the branching point, flow into the channel which extends in an oblique direction in an average manner, while repeating Brownian motion and collision with the obstacles. On the other hand, any proteins, having sizes smaller than width "l" and therefore can pass through the gaps having width "l" at the branching point, tend to flow straight. The structure of the channel is also considered so that smaller proteins will have larger probabilities of passing through the gaps between the obstacles, by arranging the obstacles so as to cut in the obliquely-extending channel. This sort of structure of the channel, as being further combined with adjustment of volume of feeding of the liquid at each of the pipe ports, is successful in separating the proteins depending on their sizes with a satisfactory resolution.

Only the three-stage arrangement was schematically shown in FIG. 11, actual arrangement preferably has an arrangement with the number of stages of 1000 or around. Also the widths of the gaps are preferably formed as being graded in the width of the gaps by the number larger than three of "l", "m" and "n". Of the widths of the gaps, "n", "m" and "l" respectively differ at the branching points 211 to 215, being made so as to be widen from the branching points 211 to branching point 215. Relations of sizes among "n", "m" and "l", however, remain constant at the individual branching points. In this embodiment, width "l" of the gaps at the branching point 211 can typically be set to 10.0 nm, width "l" of the gaps at the branching point 212 to 12.5 nm, width "l" of the gaps at the branching point 213 to 15.0 nm, width "l" of the gaps at the branching point 214 to 17.5 nm, and width "l" of the gaps at the branching point 215 to 20.0 nm.

Figure 12:
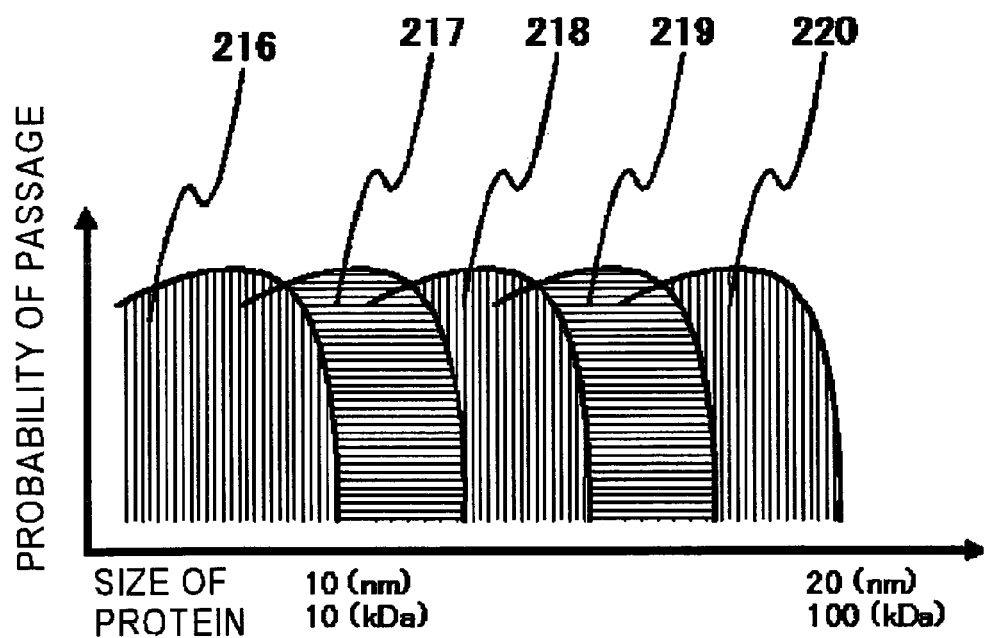
FIG. 12 is a schematic drawing showing an exemplary state of separation of proteins, for the purpose of explaining one Example of the present invention.

This sort of configuration of the particle manipulation unit makes it possible to separate proteins of 10 kDa to 100 kDa or around depending on their sizes. The smallest protein is separated at the branching point 211, and discharged out through the pipe port 206. The pipe ports 207, 208, 209 and 210 can discharge larger proteins in this order. FIG. 12 is a schematic drawing showing this way of separation. In FIG. 12, the protein separated at the branching point 211 and discharged out through the pipe port 206 is typically indicated by a region 216 ranging over the size of the protein and probability of passage. The proteins discharged out from the pipe ports 207, 208, 209 and 210aer expressed by regions 217, 218, 219 and 220, respectively.

Figure 13:
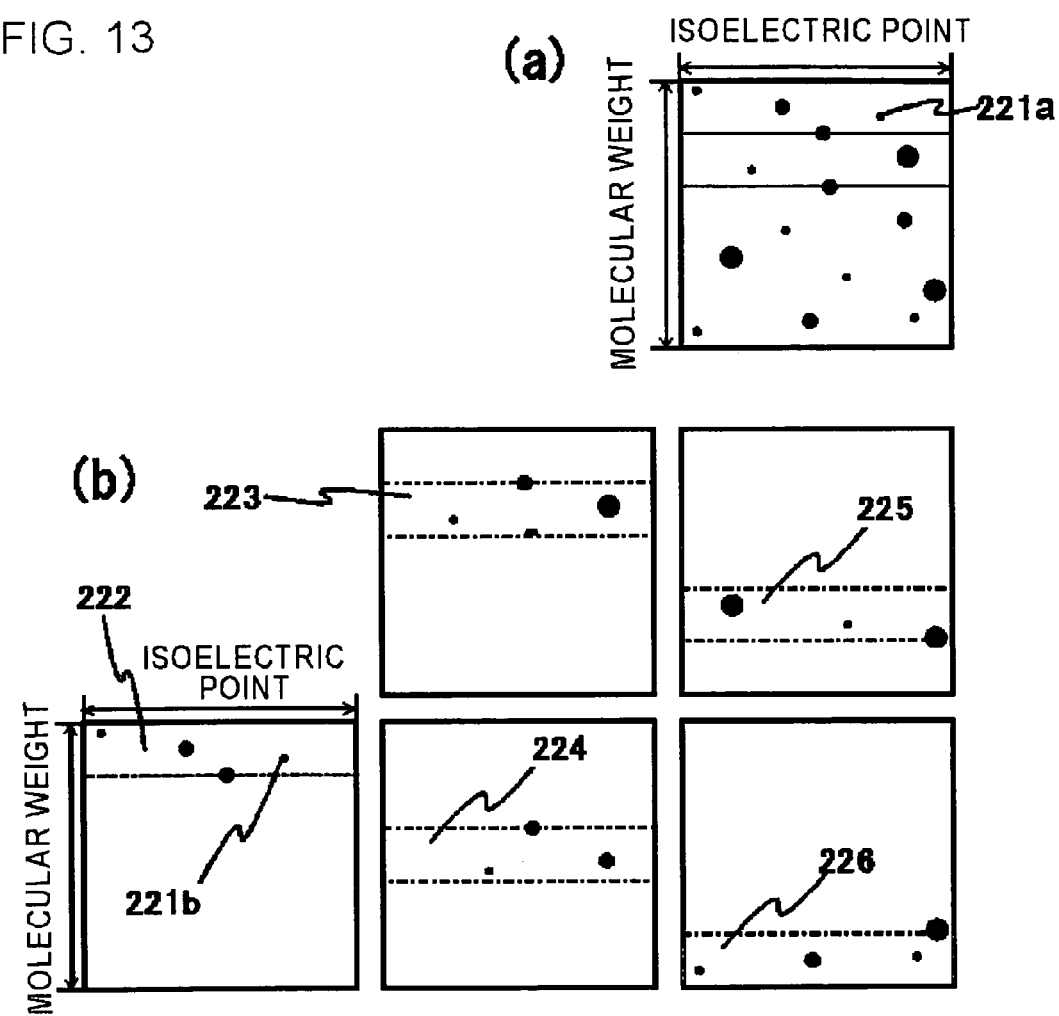
FIG. 13 is a schematic drawing showing observation of spots of proteins separated by two-dimensional electrophoresis in one Example.

Provision of such rough purification step using the above-described chip as a pretreatment of the two-dimensional electrophoresis is successful in increasing concentration of proteins in the spot relevant to the protein separated on the gel. FIG. 13 is a schematic drawing of the spots of the proteins separated by the two-dimensional electrophoresis. FIG. 13(a) shows a conventional case without rough purification step as the pre-treatment, and FIG. 13(b) shows a case with rough purification step as the pre-treatment. As shown in FIG. 13(a), the abscissa expresses separation by isoelectric point, and the ordinate expresses separation by molecular weight. Spots of the separated proteins appear on a two-dimensional map, typically as shown by a spot 221a in FIG. 13(a).

In the two-dimensional electrophoresis, a total amount of proteins chargeable for a single run of separation is limited to as much as 100 μg or around, and this generally limits the concentration of the proteins contained in the spots. Whereas adoption of the rough separation using the chip shown in FIG. 10 as the pretreatment for the two-dimensional electrophoresis makes it possible to divide the proteins into five portions depending on the sizes of the proteins which correlates to their molecular weights as shown in FIG. 12. Charging of 100 μg each of thus-divided protein samples to 5 slabs of gel results in 5 slabs of gel having protein spots formed thereon as shown in FIG. 13(b). The spots appear as being respectively localized in regions 222 to 226 indicated by dashed lines. Each of these spots contains a protein approximately 5 times as much as that of the conventional case shown in FIG. 13(a). The spot 221b may therefore be detected by a mass spectroscope, even if the amount of protein collectable from the spot 221a is extremely small and below the detection limit of the mass spectroscope.

The foregoing paragraphs have described the case where the sample separated using the chip shown in FIG. 10 was used, whereas it is, of course, allowable to use a chip comprising any of the particle manipulation units described in other modes of embodiment.

The foregoing paragraphs have described the case where the proteins were subjected to mass analysis in step 105, whereas pre-treatment using the particle manipulation unit of this embodiment is adoptable also to the case where the analysis is proceeded by using a sequencer and so forth. The particle manipulation unit used in this embodiment is by no means limited to the configuration described in the second embodiment.

Sixth Embodiment

Figure 9:
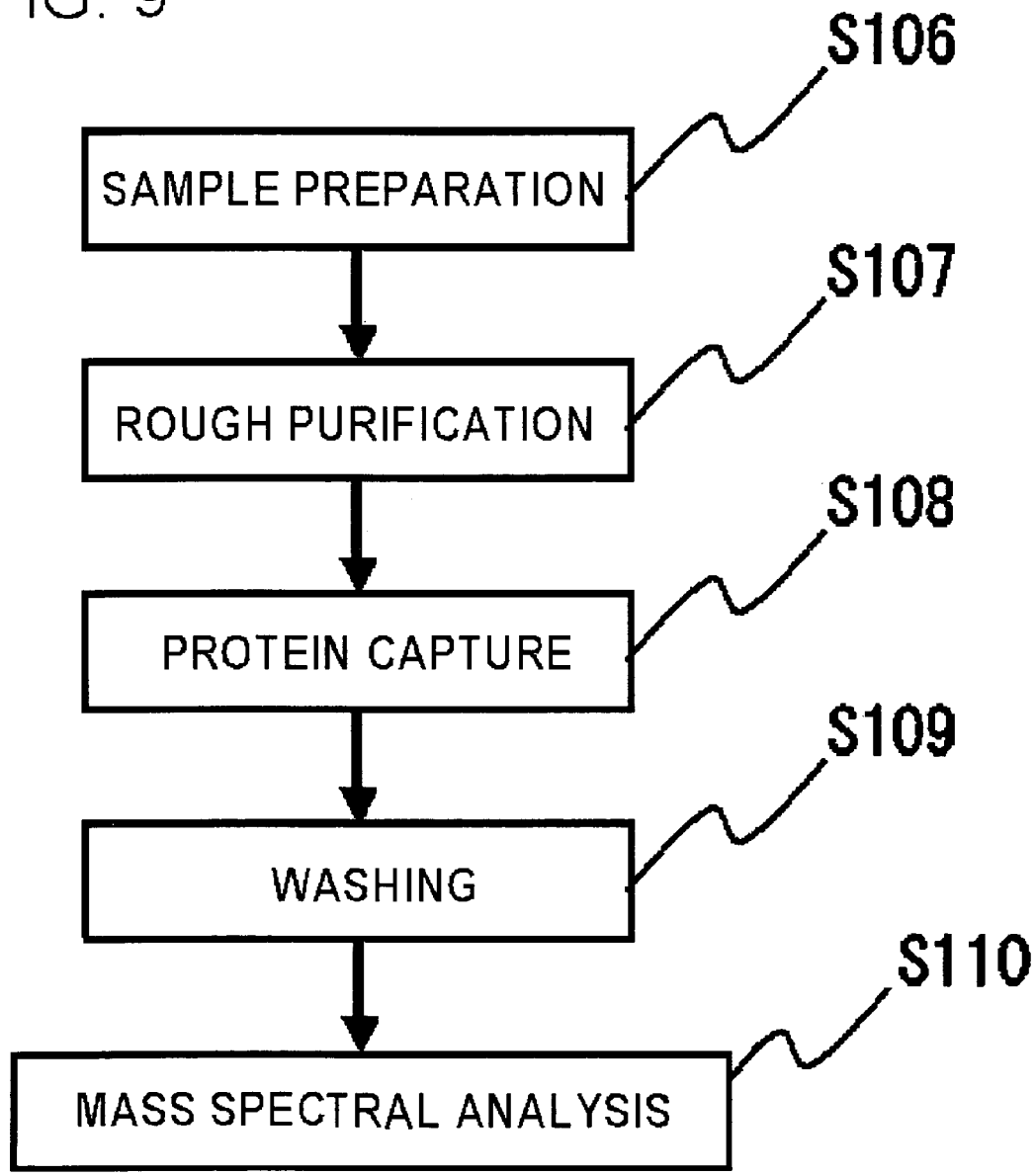
FIG. 9 is a chart showing analytical procedures of proteins of the present embodiment.

This embodiment relates to another example of particle treatment system separating specific proteins contained in a sample, and identifying them. FIG. 9 is a chart showing analytical procedures of proteins according to this embodiment.

In FIG. 9, step 106 represents a sample preparation step extracting proteins to be analyzed from cells, tissues, biological specimens or the like, and treating the obtained extract to prepare a form of sample suitable for purification using a protein chip.

Step 107 is a step of separating the proteins to be analyzed depending on their sizes using the particle manipulation unit shown in FIG. 3, described in the second embodiment.

Step 108 represents a step of adding the proteins roughly purified and separated in step 107 to the protein chip, to thereby allowing only a protein having affinity with a ligand immobilized on the chip.

Step 109 represents a washing step removing impurities such as salts and substances having no affinity remaining on the protein chip, by washing with water or a buffer solution.

Step 110 represents a step of subjecting the protein having affinity, remaining on the protein chip after step 109, to mass analysis to thereby determine the molecular weight and to identify the protein species.

The conventional method using a spin column in the rough purification step 107 has been suffering from the problems below. The protein chip is highly sensitive to proteins having relatively small molecular weights of as small as 25 KDa or below, and this was the reason for using the spin column for rough purification as the pre-treatment. It was, however, necessary for the case where the spin column was used for the pre-treatment to repeat the rough purification again, if the amount of protein obtained by the rough purification was too small to be charged on the protein chip. This has complicated the process operations, and raised difficulty in automatization.

In contrast to this, this embodiment is successful in continuously carrying out the rough purification step, which has only intermittently been permissible with the spin column, by using the particle manipulation unit shown in FIG. 3 in the rough purification step 107. This therefore makes it possible to continuously collect the target protein until a desired amount of protein for the protein chip is reached. This feature is suitable also for the automatization. Because the particle manipulation unit can be mounted on a chip, it is also allowable to integrate it with the protein chip on the same chip. This not only successful in saving labor of an operator, but also in minimizing loss of sample from step 107 to step 108. This raises an industrial advantage of achieving a high sensitivity in a general view of method of protein detection.

Seventh Embodiment

Figure 21:
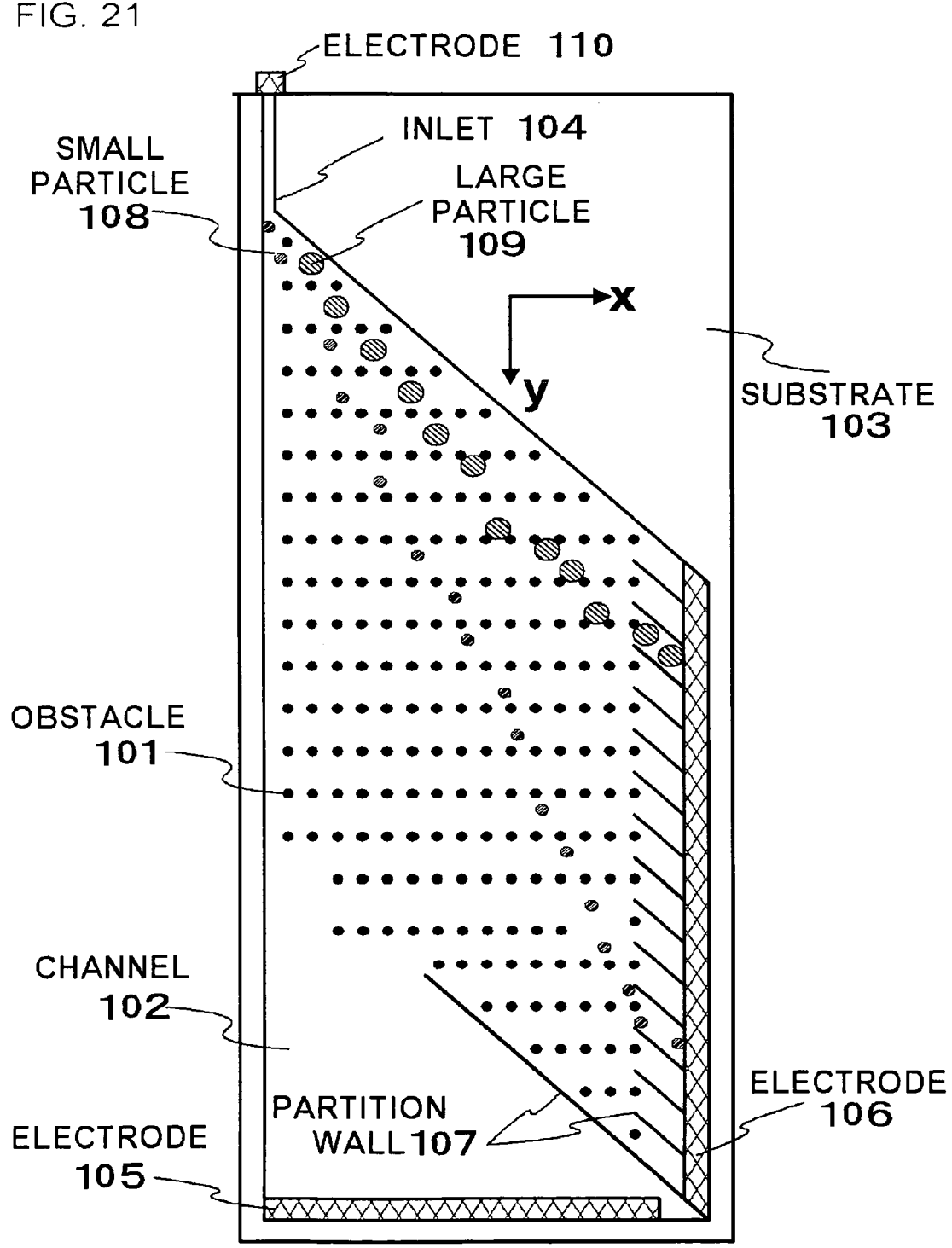
FIG. 21 is a top view showing an exemplary configuration of a particle manipulation unit of the present embodiment.

This embodiment relates to a particle manipulation unit manipulating flow of electrically-charged particles contained in a sample liquid with the aid of electric field and the obstacles formed in the channel, and guiding the electrically-charged particles depending on their sizes. FIG. 21 is a top view showing an exemplary configuration of the particle manipulation unit of this embodiment. In FIG. 21, a channel structure including obstacle 101 is fabricated on a substrate 103. x axis lies in parallel with the extending direction of a channel 102, and y axis lies normal to x axis.

In FIG. 21, rows of the obstacles 101 are disposed in parallel with the direction of x axis of the drawing, and these rows are provided to form multiple stages in the direction of y axis at regular intervals. The obstacles 101 have a columnar structure with a circular section. The obstacles 101 are arranged, as shown in the drawing, at different intervals in the transverse (x axis of the drawing) direction and in the longitudinal direction (y axis of the drawing) in the channel 102.

It is to be noted that the selection of circle as the sectional geometry of the obstacles 101 in this embodiment is a result of consideration on readiness in lithography, allowing any other sectional geometries such as square. The obstacles are preferably arranges in a matrix form such as rows disposed at regular intervals. This makes it possible to separate the particles in a more stable manner.

The particle manipulation unit of this embodiment has an electrode 110 disposed on the upstream side of an inlet 104, an electrode 106 disposed on the downstream side of the inlet 104, along the longitudinal direction of the channel 102, and an electrode 105 disposed on the downstream side of the electrode 106, so as to cross the channel 102. In FIG. 21, the electrode 105 and electrode 106 are disposed in the direction normal to each other. The electrode 105 is disposed along the wall of the channel 102 at the downstream end thereof, in the direction of x axis of the drawing, and the electrode 106 is disposed along the side wall of the channel 102, in the direction of y axis of the drawing. In the vicinity of the wall of the channel on the side opposing to the electrode 106, there is provided the inlet 104 through which the sample is introduced. In this configuration of the channel 102, width of the inlet 104 is made narrower than the region disposed on the downstream side, where flow of the particles is manipulated.

Figure 22:
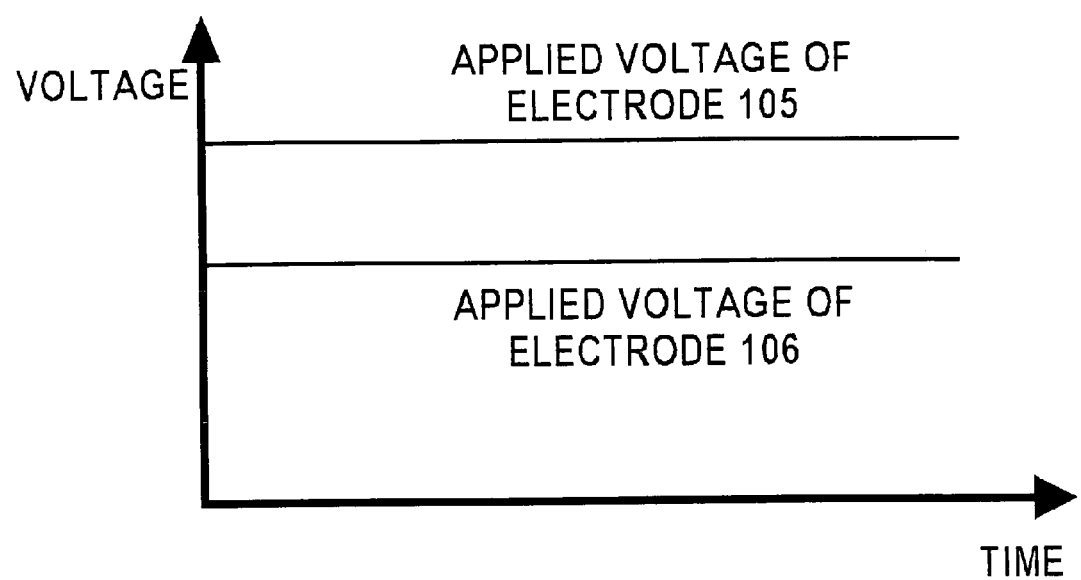
FIG. 22 is a drawing showing voltage applied to electrodes of the particle manipulation unit shown in FIG. 21.

In this channel, particles with electric charge such as DNA or SDS-treated protein are introduced through the inlet 104, and then subjected to electrophoresis. Voltage is applied herein between the electrode 110, disposed further on the upstream side of the inlet 104, the electrode 105 and the electrode 106. For an exemplary case where the particles are charged in negative, such as DNA, conditions for the voltage application, is such as shown in FIG. 22, applying positive voltage to the electrode 105 and electrode 106, assuming the electrode 110 on the upstream side as a negative electrode. It is also allowable to adjust the voltage to be applied to the electrode 105 larger than that applied to the electrode 106. This makes it possible to allow the particles to migrate predominantly in the direction of y axis of the drawing, while varying the direction of migration of the particles depending on their sizes.

Figure 23:
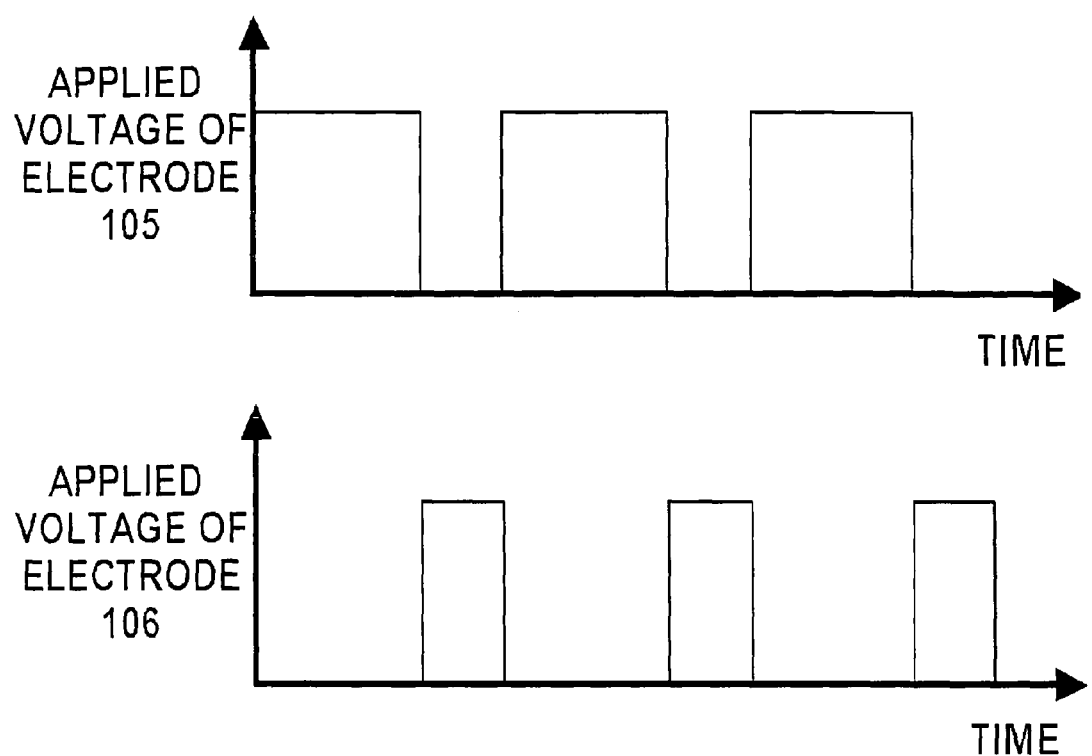
FIG. 23 is a drawing showing voltage applied to electrodes of the particle manipulation unit shown in FIG. 21.

It is also allowable, as shown in FIG. 23 and FIG. 24, to apply pulsed voltage, and to apply the pulses to the electrode 105 with a longer duration of time or with a larger number of pulses than to the electrode 106. FIG. 23 shows an exemplary case where pulse frequency is set equal between the electrode 105 and electrode 106, but duration of time of pulse voltage application is set longer for the electrode 105. FIG. 24 shows an exemplary case where pulse width of every shot is set equal between the electrode 105 and electrode 106, but the number of shot is set larger for the electrode 105. Also this case is successful in allowing the particles to predominantly migrate towards the direction of y axis of the drawing, while varying the direction of migration of the particles depending on their sizes.

Referring now back to FIG. 21, for an specific case where DC voltage is applied between the electrode 105 and electrode 106, it is preferable to dispose partition walls 107 guiding and recovering the migrated particles. The partition walls 107 can be formed along one direction, so as to serve themselves as recovery portions of the particles. In FIG. 21, a plurality of partition walls 107 are disposed on the side wall more distant from the inlet 104. The partition wall 107 are provided so as to extend from the side wall of the channel 102 towards the direction of the inlet 104. It is all enough that the partition walls 107 are arranged so as to partition the channel 102 and to fractionate the particles, even allowing horizontal alignment with x axis. Arrangement of the plurality of partition walls 107 along the longitudinal direction of the channel 102, as being inclined towards the upstream side as shown in FIG. 21, makes it possible to readily fractionate the particles migrated at different speeds, depending on their sizes.

When a sample containing small particles 108 and large particles 109 is introduced through the inlet 104 and is subjected to electrophoresis under such situation, larger particles or harder particles will have larger resistance exerted thereon by the obstacles 101. The particles having smaller diameters will migrate more fast in the direction of y axis, and those having larger diameters will migrate more slowly. On the other hand, no difference or only a small difference, unlike that in the direction of y axis, in the migration speed depending on the size of the particles will occur in the direction of x axis, because the intervals of the obstacle 101 are larger in this direction. It is preferable herein that the obstacles 101 are arranged so as to ensure width of gaps as being equivalent to the particle size in the direction of y axis, and as being larger than the particle size in the direction of x axis. The small particles 108 and large particles 109 can therefore migrate, as shown in FIG. 21, obliquely from the upper left towards the lower right, while being affected by the electric field and resistance cause by passage through the gaps between the obstacles 101. Directions of migration of the small particles 108 and large particles 109 differ herein depending on their particle sizes, allowing the large particles to migrate more closer to the direction of x axis of the drawing.

As described in the above, the particle manipulation unit shown in FIG. 21 allows the sample, introduced into the inlet 104 provided in the vicinity of one side wall of the channel 102, to migrate towards the downstream side, and at the same time towards the opposite side wall. Migration speed of the particles can be varied by the columnar obstacles 101 formed in multiple stages in the channel 102, depending on the surface property, geometry, size, deformation liability. It is therefore made possible to separate the particles in the sample depending on particle size and so forth, and to recover them between the plurality of partition walls disposed side by side on the opposite side wall along the longitudinal direction of the channel 102.

The particle manipulation unit of this embodiment can impart driving force causing migration of the particles in the sample in two directions differing from each other. Migration of the particles therefore occurs in the direction of the resultant force, if there were no obstacles 101 provided thereto. Resistance against the particles will differ depending on the intervals of the obstacles 101, diameter of the obstacles 101, radius of the particles and so forth, and this sort of difference will vary the resultant force exerted on the particles. This allows a stable separation of the particles depending on their surface property, geometry, size and deformation liability and so forth. Therefore it is made possible to separate and recover the particles at the partition walls 107 aligned side by side in a certain direction at predetermined positions in the channel 102.

Materials and methods of fabricating the particle manipulation unit of this embodiment may be the materials and methods described for example in the first embodiment. The particle manipulation unit of this embodiment has multiple stages of obstacles 101 formed in the direction of y axis, wherein the geometry of the obstacles per se can readily be fabricated using micro-fabrication technologies, configured as making it possible to more accurately control the particle flow.

This embodiment has been explained exemplifying DNA, whereas it is also made possible, when proteins for example are subjected to migration, to gather each of the proteins of different sizes into each portion of the electrode 106, and to carry out mass analysis while scanning the electrode 106 with a laser beam.

The obstacles 101 arranged in rows were arranged in the direction in parallel with x axis in the particle manipulation unit shown in FIG. 21, wherein the rows of the obstacles 101 may also be arranged as being inclined by a predetermined angle away from the x axis. The array of the obstacles is not limited to the row-wise arrangement shown in FIG. 21, but may appropriately be selected depending on migration speed of the particles, and positions of provision of the inlet 104 and partition wall 107 described later. For example, gaps between the obstacles 101 in the direction of x axis, although being kept constant for all rows in FIG. 21, may be configured so as to be narrowed from the upstream side towards the downstream side in the direction of y axis. This makes it possible to further expand a range of size of the particles to be separated.

The particles shown in FIG. 21, which were allowed to migrate by applying voltage in different directions using the electrode 104, electrode 105 and electrode 110, may be allowed to migrate under forced feeding using a pump or the like. Although the potential was generated bidirectionally in the configuration shown in FIG. 21, the number of directions in which the driving force for the migration of the particles is imparted is not limited to two, but also may be three or more.

The foregoing paragraphs have described the present invention referring to specific modes of embodiment. It is, however, obvious that the present invention is by no means limited to the above-described embodiments, and may appropriately be modified within the technical scope of the present invention. In other words, it is to be understood by those skilled in the art that these modes of embodiments are only for exemplary purposes, allowing various modifications in the individual constituents and combination of the individual fabrication steps, and that any of these modifications are included with the scope of the present invention.

For example, in the above-described modes of embodiment, it is allowable to form, as an obstacle portion interfering the particle migration, a hydrophobic region on the surface of the channel, in place of the columnar structures, and to make the residual surface, excluding the hydrophobic region, into a hydrophilic region. In this configuration, a larger molecule will more largely be interfered by the hydrophobic region, and will take a longer time to migrate. The hydrophobic region can be formed by allowing a coupling agent having a hydrophobic group to adhere on, or to bind with the surface of the substrate.

The following paragraphs will further explain the present invention referring to an Example, while being not limited thereto.

EXAMPLE

Figure 15:
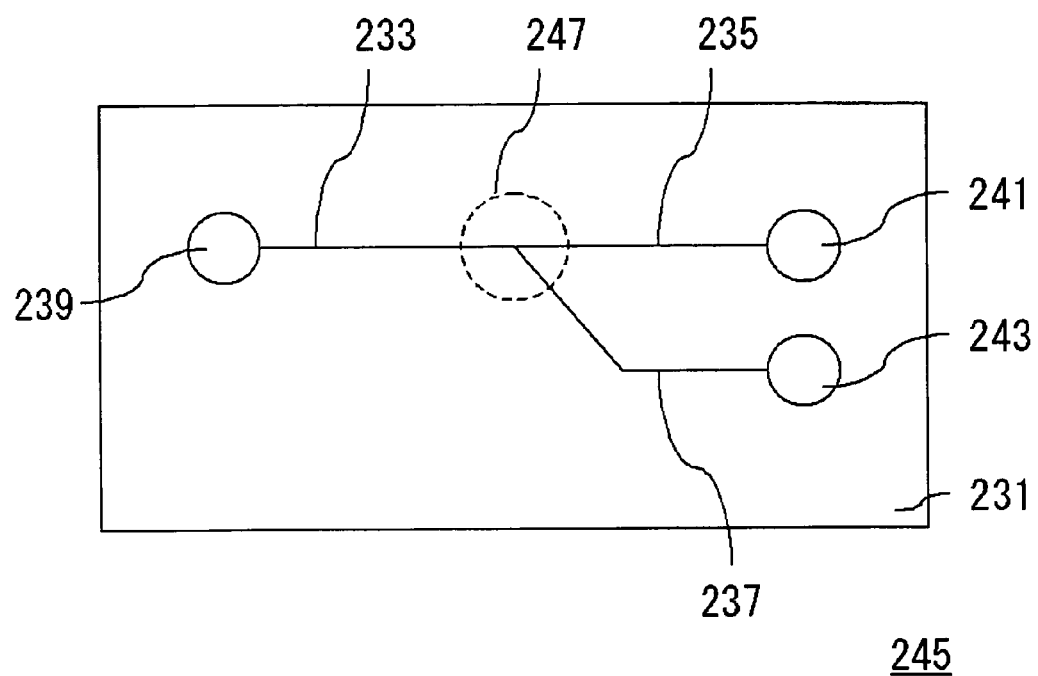
FIG. 15 is a top view showing a general configuration of a chip in one Example.

In this Example, a particle manipulation unit, in which the direction of the branched channel is laterally inverted from that in the particle manipulation unit described referring to FIG. 11, is formed on a chip, and evaluated. FIG. 15 is a top view showing a schematic configuration of the chip of this Example. In a chip 245, a main channel which comprises a channel 233 and a channel 235, and a channel 237 are formed on a substrate 231. The channel 233, channel 235 and channel 237 have a fluid reservoir 239, a fluid reservoir 241 and a fluid reservoir 243 respectively communicated therewith. The channel 233, channel 235 and channel 237 communicate with each other at a branching point 247 indicated by a dotted line in the drawing. The fluid reservoir 239, fluid reservoir 241 and fluid reservoir 243 respectively have an electrode (not shown) formed therein by inserting a platinum line (not shown).

Figure 16:
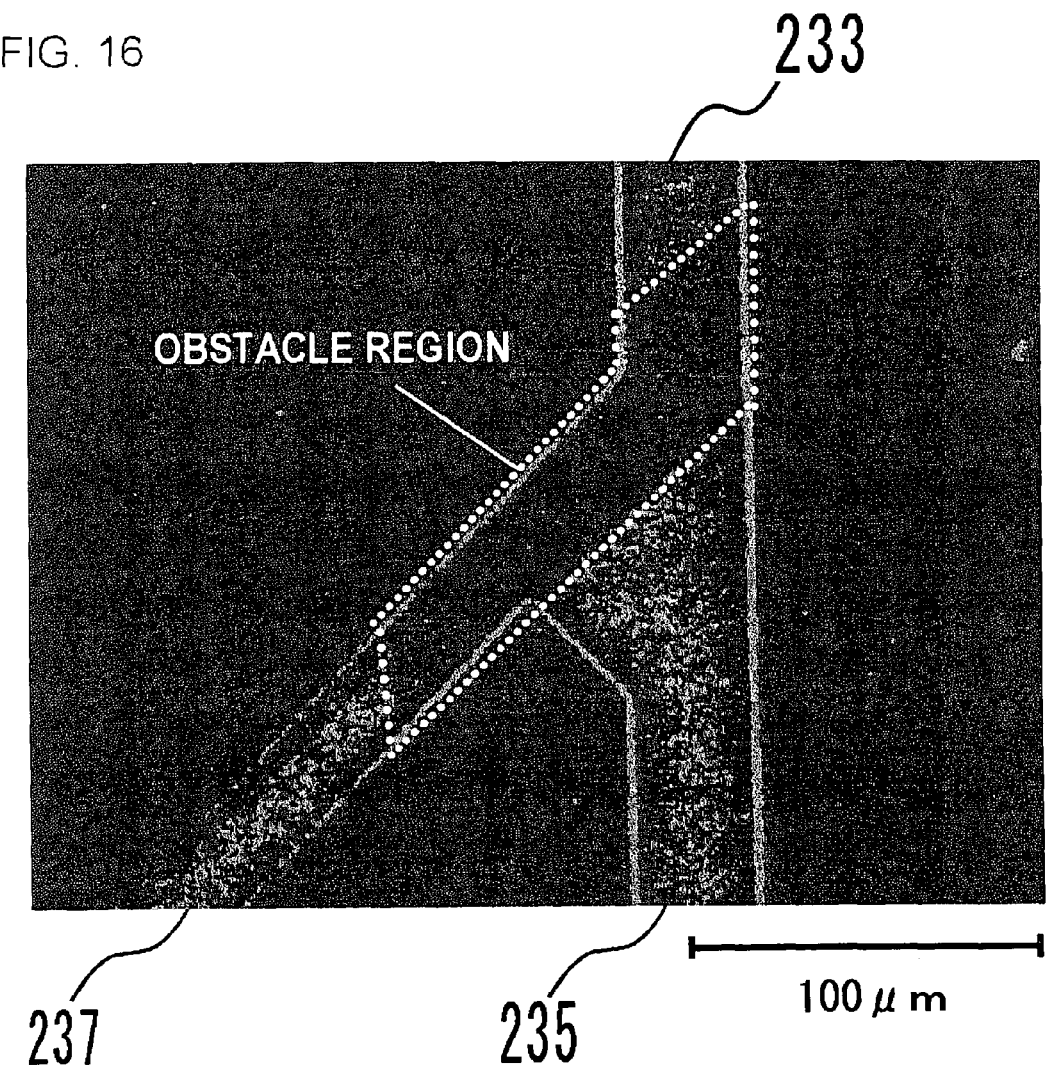
FIG. 16 is a drawing showing a configuration of a branching point of a chip in one Example.

In this Example, the particle manipulation unit was fabricated by adopting the fabrication method described in the fifth embodiment. FIG. 16 is a drawing showing a microscopic image of the branching point 247 of the fabricated particle manipulation unit. Although being laterally inverted in the direction of the branched channel, it is obvious that the configuration corresponds with the particle manipulation unit schematically shown in FIG. 11. Width of the channel 233 and channel 235 in FIG. 16 was set to 40 µm. Arrays of the obstacles were formed with the number of stages of 1000 or around in the obstacle region shown in the drawing.

Figure 17:
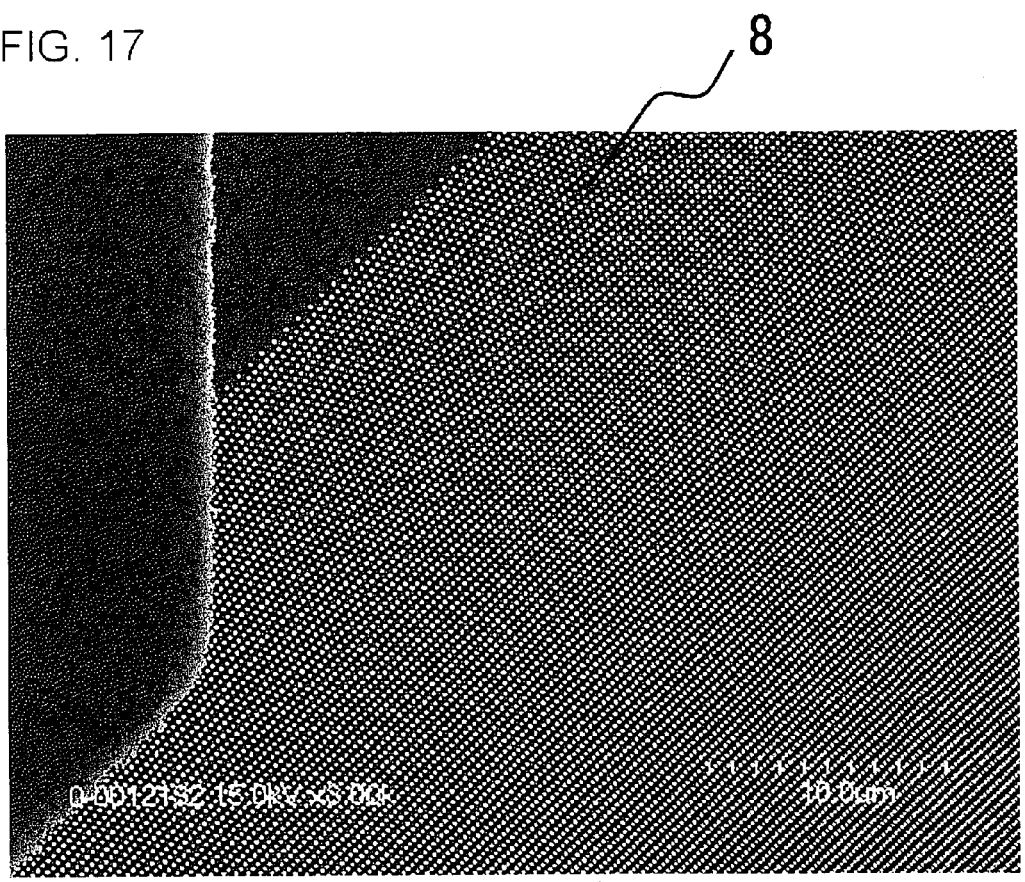
FIG. 17 is a drawing showing a configuration of an obstacle region of a chip in one Example.
Figure 18:
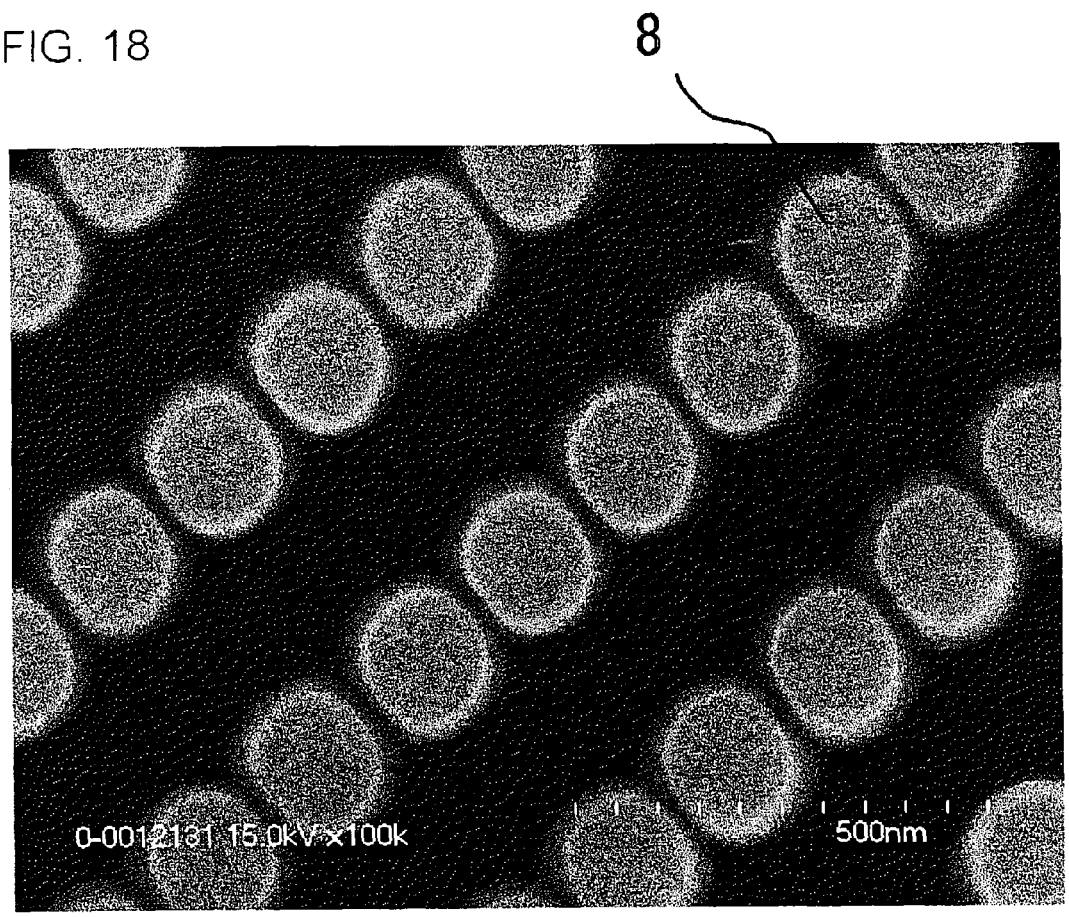
FIG. 18 is a drawing showing a configuration of an obstacle region of a chip in one Example.

FIG. 17 is a drawing showing a scanning electron microscopic image of the obstacle region. Every white dot corresponds to the obstacle 8. Gaps between the obstacle 8 are made gradually narrower towards the downstream side of the branching point. More specifically, FIG. 17 is a scanning electron microscopic image of a portion on the downstream side of the branching point and facing to the channel 237. The gaps between the obstacles 8, which correspond to reference mark "l" in FIG. 11, is set to 32 nm or around, and gaps corresponded to "n" is set to 150 nm. On the other hand, gaps which correspond to reference mark "o" in FIG. 11, is set to approximately 150 nm. FIG. 18 is a drawing showing an enlarged electron microscopic image of the array structure of the obstacles 8 formed in the obstacle region.

In this Example, DNA was manipulated as described below, using the particle manipulation unit.

DNA dyed with phosphorescence was subjected to electrophoresis in the channel filled with a buffer solution, and observed. Electrophoresis was proceeded while respectively applying a voltage of −5 V to the channel 233, 18 V to the channel 235, and 1.5 V to the channel 237.

Figure 19:
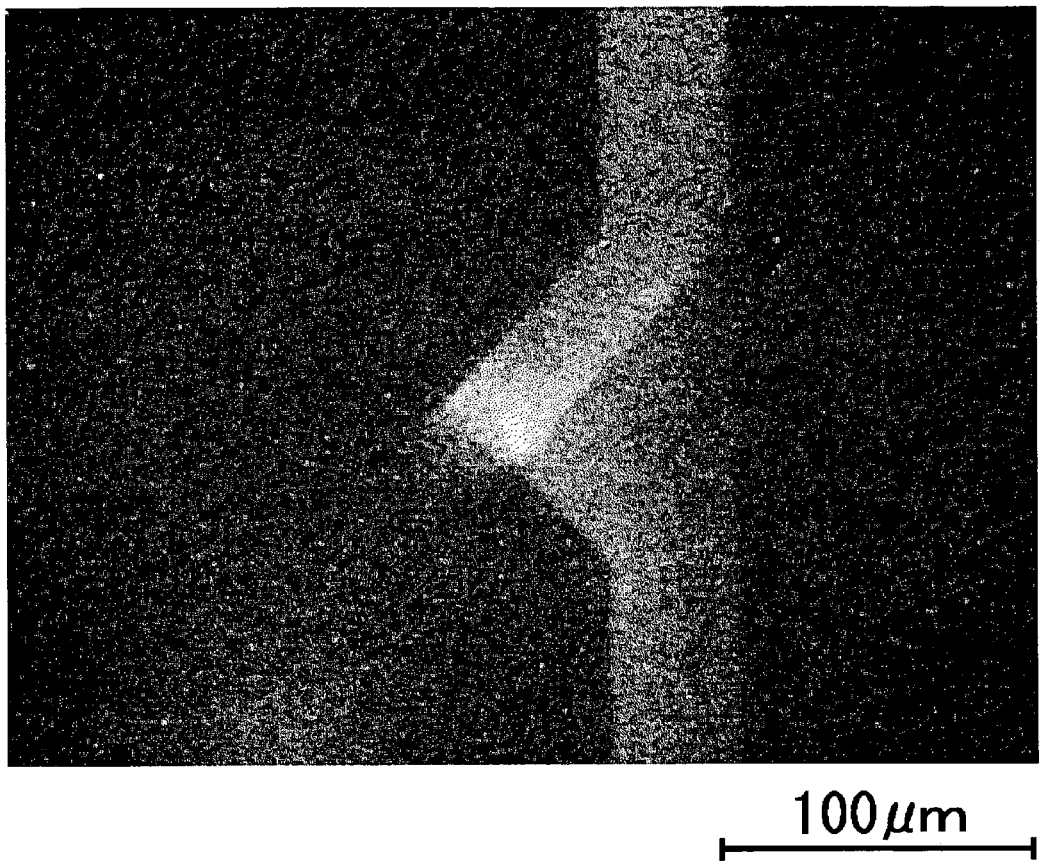
FIG. 19 is a drawing showing a result of electrophoresis of a 100-bp DNA on a particle manipulation unit in one Example.

FIG. 19 is a phosphorescent microscopic image of a 100 bp DNA obtained after the electrophoresis, observed under the same field with FIG. 16. In FIG. 19, every white dot corresponds to each particle of the phosphorescent dyed DNA. Most of DNA particles are found to flow through the gaps of approximately 32 nm wide into the channel 235, without migrating towards the channel 237. According to description of P. G. Righetti, "Capillary Electrophoresis in Analytical Biotechnology", 1996, CRC Press, Inc., p. 480, gyration radius of DNA can be calculated by the equation (1) below:

$$\langle r^2 \rangle = \frac{1}{12}b^2\left(\frac{2N}{330} - 1 + e^{\frac{-2N}{330}}\right) \tag{1}$$

(in the equation (1), r represents gyration radius, b represents Kuhn length, which is 100 nm herein. N expresses the number of base pairs of the DNA.)

Using the gyration radius calculated by the above equation (1), particle size of the 100 bp DNA calculated using the gyration radius was found to be approximately 22 nm, which was considered to be further reduced if the deformation liability thereof under the conditions for voltage application in the buffer solution is taken into consideration, suggesting passage through the gaps of approximately 32 nm wide.

Figure 20:
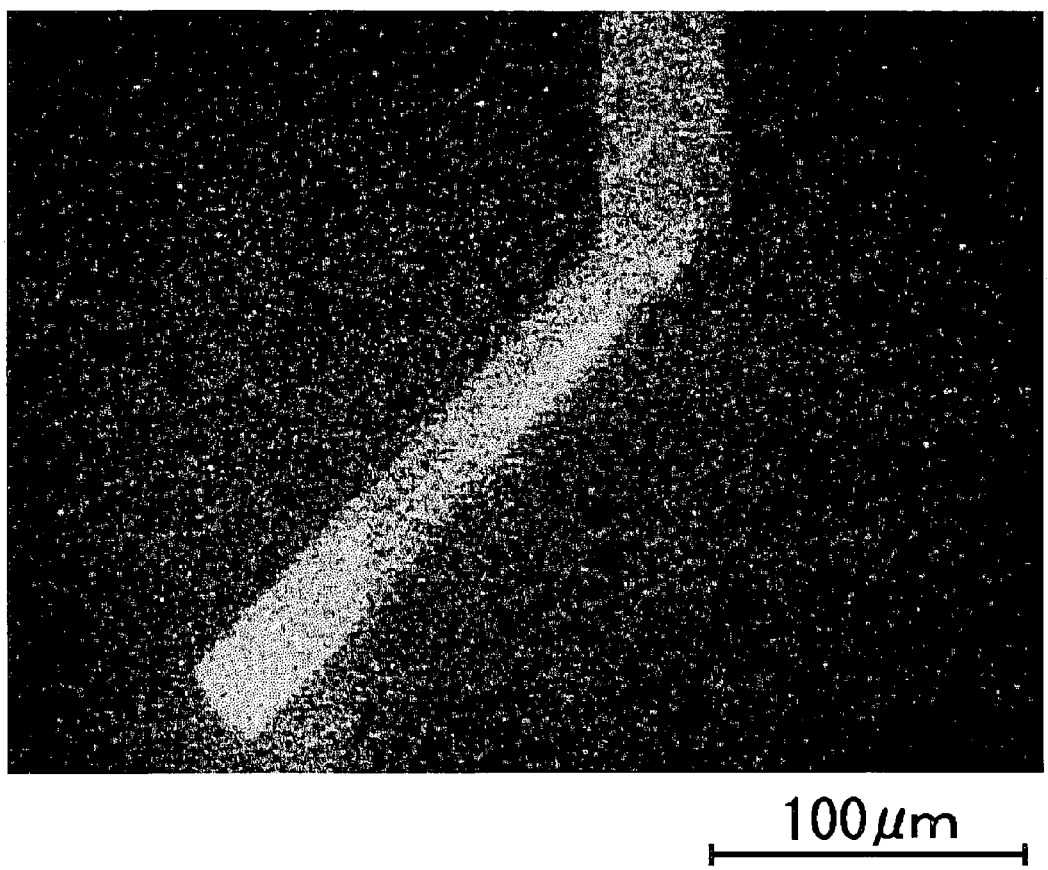
FIG. 20 is a drawing showing a result of electrophoresis of a 300-bp DNA on a particle manipulation unit in one Example.

FIG. 20 is a drawing showing a phosphorescence microscopic image of 300 bp DNA after electrophoresis under the same conditions for voltage application. The DNA was found to flow towards the channel 237 without passing through the gaps of approximately 32 nm wide. It is to be noted herein that the particle size calculated by the above equation (1) using the gyration radius of the 300 bp DNA is approximately 57 nm, which is sufficiently larger than the particle size in consideration of deformation liability of the DNA under the conditions for voltage application of this Example, suggesting rejection of passage through the gaps of approximately 32 nm wide.

As has been described in the above, this Example is successful in realizing the particle manipulation unit capable of manipulating direction of flow of DNAs depending on the size thereof. It was also made possible to separate the DNAs using the particle manipulation unit of this Example.

What is claimed is:

1. A particle manipulation unit, comprising:
   a substrate;
   a channel formed on said substrate, comprising a first channel and a second channel branched out from said first channel, capable of manipulating direction of flow of particles flowing in a liquid in said channel; and
   a permeation limiting zone limiting permeation of at least a part of said particles, disposed in said first channel in the vicinity of a branching point where one or more second channels are branched out from said first channel,
   wherein said permeation limiting zone has a plurality of obstacles arranged to be spaced from each other, the obstacles being selected from the group consisting of cylinders, pseudo-cylinders, cones, circular cones, elliptical cones, prisms, triangular prisms and quadrangular prisms,
   a gap between adjacent obstacles is set to a size allowing a part of said particles to permeate therethrough, and said obstacles are arranged so that a direction of force causing flow of said particles lies non-normal to and non-parallel with a direction of arrangement of said obstacles at the front-most plane on the branching point side of said permeation limiting zone.

2. The particle manipulation unit according to claim 1, wherein said plurality of obstacles are configured so as to control direction of flow of said particles, and so as to guide at least a part of said particles to either of said first channel and said second channel, depending on the arrangement thereof.

3. The particle manipulation unit according to claim 1, wherein said obstacles are periodically arranged in a two-dimensional manner.

4. The particle manipulation unit according to claim 1, wherein said particles contain any one of polymer resin, metal, semiconductor and biological molecules.

5. The particle manipulation unit according to claim 1, having a function of separating said particles depending on their sizes.

6. The particle manipulation unit according to claim 1, having a function of introducing a suspension, having said particles suspended therein, into said channel and diluting said suspension.

7. The particle manipulation unit according to claim 1, having a function of introducing a suspension, having said particles suspended therein, into said channel and desalting said suspension.

8. A chip having the particle manipulation unit described in claim 1.

9. A detection device comprising said chip described in claim 8 and a detection unit for said particles.

10. The detection device according to claim 9, wherein said detection unit for said particles is configured by a mass spectroscope.

11. A method of separating proteins comprising two or more process steps respectively using separation means differing from each other,
   having, as one of said process steps separating proteins, a process step separating proteins using the chip according to claim 8 having at least a function of continuously separating proteins.

12. A method of detecting proteins in which proteins are separated by the method of separating proteins described in claim 11, the separated proteins are decomposed by protease treatment, and the decomposed products are identified using a mass spectroscope.

13. A method of separating proteins comprising two or more process steps respectively using separation means differing from each other,
   having, as one of said process steps separating proteins, a process step roughly separating proteins using a chip described in claim 8.

14. A method of capturing proteins in which proteins are separated using the chip described in claim 8, and a target protein is captured from a suspension of a plurality of proteins, making use of affinity.

15. A method of detecting proteins in which the target protein is captured by the method of capturing proteins described in claim 14, the surface of the chip is washed, and the captured protein is identified using a mass spectroscope.

16. The particle manipulation unit according to claim 1, wherein said particles satisfying an angle between 0° and 90° to the obstacles never clog gaps in the obstacles.

17. A particle manipulation unit, comprising:
   a substrate;
   a channel formed on said substrate, comprising a main channel, and one or more side channels branched out from said main channel towards the downstream side of said main channel, capable of manipulating direction of flow of particles flowing in a liquid in said channel;
   a flow control portion disposed on the upstream side of a branching point where one or more side channels are branched out from said main channel,
   said flow control portion controlling direction of flow of said particles, and guiding at least a part of said particles to either of said main channel and said side channel,
   wherein said flow control portion has a plurality of obstacles periodically arranged, said plurality of obstacles being configured so as to control direction of flow of said particles, and so as to guide at least a part of said particles to either of said main channel and said side channels, depending on the arrangement thereof,
   the obstacles are selected from the group consisting of cylinders, pseudo-cylinders, cones, circular cones, elliptical cones, prisms, triangular prisms and quadrangular prisms, and
   the obstacles are arranged so that a direction of force causing flow of said particles lies non-normal to and non-parallel with a direction of arrangement of said obstacles at a front-most plane on a branching point side of a permeation limiting zone.

18. The particle manipulation unit according to claim 17, wherein a gap between the adjacent obstacles of said flow control portion in the direction of formation of said main channel differs from that in the direction of formation of said side channel.

19. The particle manipulation unit according to claim 17, wherein said particles satisfying an angle between 0° and 90° to the obstacles never clog gaps in the obstacles.

20. A particle manipulation unit, comprising:
   a substrate; and
   a channel formed on said substrate, capable of manipulating state of flow of particles flowing in said channel, said channel having a flow control portion which comprises trenches formed on the wall surface of said channel, guiding at least a part of said particles to a predetermined direction,
   wherein said trench structures have a long axis and a short axis oriented neither in parallel nor in normal to a force causing the flow of particles.

21. The particle manipulation unit according to claim 20, having the flow control portion which comprises trenches periodically formed on the wall surface of said channel.

22. The particle manipulation unit according to claim 21, wherein said flow control portion comprises a plurality of periodic patterns which differ in geometry of opening of said trenches or pitch of said trench.

23. The particle manipulation unit according to claim 22, wherein said plurality of periodic patterns are formed with mirror symmetry in said flow control portion.

24. A particle manipulation unit comprising a substrate, and a channel formed on said substrate, capable of manipulating direction of flow of particles flowing in said channel, said channel having, provided thereto, a permeation limiting zone limiting permeation therethrough of at least a part of said particles, said permeation limiting zone having a width of entrance narrower than the width of said permeation limiting zone, having a first drive means providing said particle flowing in said permeation limiting zone with a migration speed in one direction, and a second drive means providing a migration speed in other direction different from said one direction, and said permeation limiting zone being provided with a plurality of obstacles arranged as being spaced from each other, wherein the obstacles are selected from the group consisting of cylinders, pseudo-cylinders, cones, circular cones, elliptical cones, prisms, triangular prisms and quadrangular prisms, and the obstacles are arranged so that a direction of force causing flow of said particles lies non-normal to and non-parallel with a direction of arrangement of said obstacles at a front-most plane on a branching point side of the permeation limiting zone.

25. The particle manipulation unit according to claim 24, wherein said particles satisfying an angle between 0° and 90° to the obstacles never clog gaps in the obstacles.

* * * * *